(12) United States Patent
Vacca

(10) Patent No.: US 9,551,645 B2
(45) Date of Patent: Jan. 24, 2017

(54) FLOW CYTOMETRY APPARATUS AND METHODS

(71) Applicant: Kinetic River Corp., Cupertino, CA (US)

(72) Inventor: Giacomo Vacca, Campbell, CA (US)

(73) Assignee: Kinetic River Corp., Cupertino, CA (US)

( * ) Notice: Subject to any disclaimer, the term of this patent is extended or adjusted under 35 U.S.C. 154(b) by 5 days.

(21) Appl. No.: 14/793,626

(22) Filed: Jul. 7, 2015

(65) Prior Publication Data

US 2016/0011096 A1    Jan. 14, 2016

Related U.S. Application Data

(60) Provisional application No. 62/022,662, filed on Jul. 10, 2014.

(51) Int. Cl.
*G01N 15/14* (2006.01)
*G01N 15/10* (2006.01)

(52) U.S. Cl.
CPC ...... *G01N 15/1436* (2013.01); *G01N 15/1404* (2013.01); *G01N 2015/1006* (2013.01); *G01N 2015/149* (2013.01); *G01N 2015/1415* (2013.01)

(58) Field of Classification Search
CPC . G01N 15/1404; G01N 15/1436; G01N 21/00
USPC ....................................................... 356/342
See application file for complete search history.

(56) References Cited

U.S. PATENT DOCUMENTS

| 4,983,038 | A | | 1/1991 | Ohki et al. | |
|---|---|---|---|---|---|
| 5,007,732 | A | * | 4/1991 | Ohki | G01N 15/1404 356/39 |
| 5,690,895 | A | * | 11/1997 | Matsumoto | G01N 15/1404 356/246 |
| 6,819,411 | B1 | | 11/2004 | Sharpe et al. | |
| 7,221,453 | B2 | | 5/2007 | Sharpe et al. | |
| 7,586,604 | B2 | | 9/2009 | Sharpe et al. | |
| 7,929,137 | B2 | | 4/2011 | Sharpe et al. | |

(Continued)

OTHER PUBLICATIONS

International Search Report mailed Oct. 6, 2015 from International Application No. PCT/US2015/039566, 12 pgs.

(Continued)

*Primary Examiner* — Roy M Punnoose
(74) *Attorney, Agent, or Firm* — Aurora Consulting LLC

(57) ABSTRACT

A particle analyzer, comprising a source of a substantially nondiffracting light beam; a flow path configured to produce in a flowcell a ribbon-like core stream having a cross-sectional aspect ratio of at least 4 and a largest cross-sectional dimension of at least 50 micrometers; the flowcell being configured to expose a segment of the core stream to the light beam; a detector configured to receive a signal resulting from an interaction of a particle in the core stream with the light beam; a first sorting actuator connected with the flowcell, downstream of the exposed segment of core stream; a plurality of sorting channels in fluid connection with the flow path and downstream of the first actuator; the actuator having multiple actuation states, each state configured to direct at least one part of the core stream to a corresponding channel; a second sorting actuator connected with the flowcell, opposite the first actuator, and operable in coordination with the first actuator.

15 Claims, 21 Drawing Sheets

(56) References Cited

U.S. PATENT DOCUMENTS

| | | | |
|---|---|---|---|
| 8,004,661 | B2 | 8/2011 | Luscher |
| 8,535,536 | B1 | 9/2013 | Gale et al. |
| 9,429,524 | B2 * | 8/2016 | Wanders ............ G01N 15/1404 |
| 2002/0036258 | A1 | 3/2002 | Bergstein et al. |
| 2002/0094685 | A1 | 7/2002 | Nakata et al. |
| 2005/0110996 | A1 | 5/2005 | Sharpe et al. |
| 2006/0062698 | A1 | 3/2006 | Foster et al. |
| 2007/0036678 | A1 * | 2/2007 | Sundararajan ...... B01F 13/0062 422/68.1 |
| 2007/0285662 | A1 | 12/2007 | Sharpe et al. |
| 2011/0204257 | A1 | 8/2011 | Wiseman et al. |
| 2013/0208332 | A1 | 8/2013 | Yu et al. |

OTHER PUBLICATIONS

Baumgartl et al., "Far Field Subwavelength Focusing Using Optical Eigenmodes", Applied Physics Letters, vol. 98, 181109, May 6, 2011, 3 pgs.

Bouchal et al., "Propagation-invariant electromagnetic fields: Theory and experiment", Journal of Modern Optics, 1996, vol. 43, No. 9, pp. 1905-1920.

T.Čižmár et al., "Interference-Free Superposition of Nonzero Order Light Modes: Functionalized Optical Landscapes," Applied Physics Letters, vol. 98, 081114 (2011), 3 pgs.

Cupp et al., "Rare-Event Analysis Methods for Detection of Fetal Red Blood Cells in Maternal Blood", Cytometry, vol. 5, 1984, pp. 138-144.

K. Dholakia et al., "Shaping the Future of Manipulation," Nature Photonics, vol. 5, Jun. 2011, pp. 335-342.

Donnenberg et al., "Rare-Event Analysis in Flow Cytometry", Clinics in Laboratory Medicine, vol. 27, 2007, pp. 627-652.

Durnin et al., "Diffraction-Free Beams," Physical Review Letters, vol. 58, No. 15, Apr. 13, 1987, pp. 1499-1501.

Keij et al., "Coincidence in High-Speed Flow Cytometry: Models and Measurements", Cytometry, vol. 12, 1991, pp. 398-404.

Mercer, "Calibration of Coulter Counters for Particles 1 in Diameter", The Review of Scientific Instruments, vol. 37, No. 11, Nov. 1966, pp. 1515-1520.

Stevenson et al., "Single Cell Optical Transfection", Journal of the Royal Society Interface, vol. 7, 2010, pp. 863-871.

Nagrath et al., "Isolation of Rare Circulating Tumour Cells in Cancer Patients by Microchip Technology", Nature Letters, vol. 450, Dec. 20-27, 2007, pp. 1235-1241.

Tsampoula et al., "Femtosecond Cellular Transfection Using a Nondiffracting Light Beam", Applied Physics Letters, vol. 91, 2007, 3 pgs.

* cited by examiner 201 light propagation

FLOW CYTOMETRY APPARATUS AND METHODS

BACKGROUND

Cellular analysis by flow cytometry has reached a high level of both sophistication and parallelism, enabling its widespread use in life science research and medical diagnostics alike. Yet for all its remarkable success as a technology, much remains to be done in order to meet significant needs in terms of applications.

One of the areas where flow cytometry has not yet made significant inroads, but could potentially bring tremendous benefit, is the analysis of very rare events. The diagnostic/prognostic fields of Circulating Tumor Cells (CTCs) and detection of fetal cells in maternal blood are well-known examples of what could be called ultra-rare-event analysis; here the "interesting" cells make up a minute fraction of the total cells in the sample. For example, out of the ~$10^9$ cell/mL concentration of normal cells in blood, CTCs with clinical significance can range from $10^5$ to less than 1 cell/mL. Additionally, current technology based on surface-antigen binding (whether magnetically mediated or not) will, by design, miss cell populations not defined by surface antigens. Missing relevant cells is particularly serious in CTC analysis, where false negatives can, at best, reduce assay effectiveness, and at worst, contribute to higher patient mortality. Since flow cytometry is not restricted to surface-antigen recognition, but can additionally identify cells based on intracellular markers (e.g., vimentin or cytokeratin, for mesenchymal cells), nucleic-acid content, and even morphology, it could come to the rescue; that it has largely not, so far, is an indictment of its current limitations in terms of volumetric sample delivery and analytical throughput with regards to rare-event analysis.

If one were able to break through the current technology limitations in flow cytometry and deliver drastically improved volumetric throughput ("extreme throughput"), a number of benefits would result. In the example of rare-event analysis for CTCs, one could envision executing a protocol in minutes instead of hours or even days, significantly reducing the costs of diagnosis and monitoring; more importantly, testing simply not done today would all of a sudden become practical (and affordable) to execute. This innovation would radically simplify existing workflow by allowing the rapid, routine analysis of patient specimens, avoiding the majority of the complex sample preparation steps involved in current practice. Additionally, there would be more transformational changes involved in applying the proposed approach to rare-event analysis than just boosting throughput to extreme levels (in itself sufficient motivation). By bringing the analysis rate of flow cytometry up to the level of immunocapture-based technologies for CTC applications, one would not simply add another analytical modality to the mix: one would leverage five decades of platform and assay development. Flow cytometry has shown a remarkable ability to adapt over time to evolving scientific findings: As new markers emerge, as new cellular identification strategies are identified and developed, flow-based protocols have been quick to incorporate the new possibilities into the technology and the discipline. The result is a stunningly flexible set of tools that can be used to count, identify, analyze, characterize, select, and (by sorting) harvest and purify desired cells in a mix. Bringing this toolset to bear in the emerging field of CTC analysis would present tremendous opportunities to researchers and, ultimately, clinicians in their efforts to understand, control, and fight cancer. Specifically, an extreme throughput analyzer would allow CTC detection (and ultimately, capture) based on multiple selection criteria, criteria updateable over time, and would do so faster, more reliably, and with simpler sample preparation than with currently available technologies. Ultimately, it is expected that such an analyzer, by returning more accurate results and providing an earlier, more sensitive detection of the metastatic process, could help to significantly improve the survival odds of cancer patients.

More broadly, the development of an extreme-throughput flow cytometry technology platform relying on familiar, established assay and protocol formats would make the tool attractive not only for research laboratories, but also in the context of High-Throughput Screening (HTS) for pharmaceutical development, as well as in clinical environments performing generally routine flow-based tests—again, by drastically speeding up performance, by simplifying the sample preparation procedure, and by delivering improved sensitivity.

SUMMARY

A particle analyzer, comprising:
a source of a non-Gaussian, substantially nondiffracting light beam;
a flow path configured to produce a ribbon-like core stream in a flowcell, said core stream having a cross-sectional aspect ratio of at least 4 and a largest cross-sectional dimension of at least 50 micrometers;
said flowcell being configured to expose a segment of said core stream to said light beam; and
a detector configured to detect a signal from said core stream, the signal resulting from an interaction of a particle in said core stream with said light beam.

A particle analyzer, comprising:
a source of a non-Gaussian, substantially nondiffracting light beam;
a flow path configured to produce a ribbon-like core stream in a flowcell, said core stream having a cross-sectional aspect ratio of at least 4 and a largest cross-sectional dimension of at least 50 micrometers;
said flowcell being configured to expose a segment of said core stream to said light beam;
a detector configured to detect a signal from said core stream, the signal resulting from an interaction of a particle in said core stream with said light beam;
a first sorting actuator connected with said flowcell and downstream of said segment of said core stream exposed to said light beam; and
a plurality of sorting channels in fluid connection with said flow path and downstream of said first sorting actuator;
said first sorting actuator having multiple actuation states, each actuation state configured to direct at least one part of said core stream to a corresponding sorting channel of said plurality of sorting channels.

A particle analyzer, comprising:
a source of a non-Gaussian, substantially nondiffracting light beam;
a flow path configured to produce a ribbon-like core stream in a flowcell, said core stream having a cross-sectional aspect ratio of at least 4 and a largest cross-sectional dimension of at least 50 micrometers;
said flowcell being configured to expose a segment of said core stream to said light beam;

a detector configured to detect a signal from said core stream, the signal resulting from an interaction of a particle in said core stream with said light beam;

a first sorting actuator connected with said flowcell and downstream of said segment of said core stream exposed to said light beam; and a plurality of sorting channels in fluid connection with said flow path and downstream of said first sorting actuator;

said first sorting actuator having multiple actuation states, each actuation state configured to direct at least one part of said core stream to a corresponding sorting channel of said plurality of sorting channels; and a second sorting actuator, said second sorting actuator being connected with said flowcell and opposite said first sorting actuator, said second sorting actuator being operable in coordination with said first sorting actuator.

A particle analyzer, comprising:

a source of a non-Gaussian, substantially nondiffracting light beam;

a flow path configured to produce a ribbon-like core stream in a flowcell, said core stream having a cross-sectional aspect ratio of at least 4 and a largest cross-sectional dimension of at least 50 micrometers;

said flowcell being configured to expose a segment of said core stream to said light beam; and a detector configured to detect a signal from said core stream, the signal resulting from an interaction of a particle in said core stream with said light beam;

wherein said light beam is aligned with the largest cross-sectional dimension of said core stream under an angle of no more than 45 degrees.

A particle analyzer, comprising:

a source of a non-Gaussian, substantially nondiffracting light beam;

a flow path configured to produce a ribbon-like core stream in a flowcell, said core stream having a cross-sectional aspect ratio of at least 4 and a largest cross-sectional dimension of at least 50 micrometers;

said flowcell being configured to expose a segment of said core stream to said light beam; and a detector configured to detect a signal from said core stream, the signal resulting from an interaction of a particle in said core stream with said light beam;

wherein said light beam is aligned substantially along the largest cross-sectional dimension of said core stream.

A particle analyzer, comprising:

a source of a non-Gaussian, substantially nondiffracting light beam;

a flow path configured to produce a ribbon-like core stream in a flowcell, said core stream having a cross-sectional aspect ratio of at least 4 and a largest cross-sectional dimension of at least 50 micrometers;

said flowcell being configured to expose a segment of said core stream to said light beam; and a plurality of detectors, whereby individual detectors in said plurality of detectors are configured to receive a signal from a corresponding portion of said core stream, said signal resulting from an interaction of a particle in said corresponding portion of said core stream with said light beam.

A particle analyzer, comprising:

a source of a non-Gaussian, substantially nondiffracting light beam;

a flow path configured to produce a ribbon-like core stream in a flowcell, said core stream having a cross-sectional aspect ratio of at least 4 and a largest cross-sectional dimension of at least 50 micrometers;

said flowcell being configured to expose a segment of said core stream to said light beam;

a plurality of detectors, whereby individual detectors in said plurality of detectors are configured to receive a signal from a corresponding portion of said core stream, said signal resulting from an interaction of a particle in said corresponding portion of said core stream with said light beam;

a first plurality of sorting actuators connected with said flowcell, said first plurality of sorting actuators being positioned downstream of said segment of said core stream exposed to said light beam;

said first plurality of sorting actuators being in substantial alignment with the largest cross-sectional dimension of said core stream; and a plurality of sorting channels in fluid connection with said flow path and downstream of said first plurality of sorting actuators;

the sorting actuators of said first plurality of sorting actuators having multiple actuation states, each actuation state configured to direct at least one part of said core stream to a corresponding sorting channel of said plurality of sorting channels.

A particle analyzer, comprising:

a source of a non-Gaussian, substantially nondiffracting light beam;

a flow path configured to produce a ribbon-like core stream in a flowcell, said core stream having a cross-sectional aspect ratio of at least 4 and a largest cross-sectional dimension of at least 50 micrometers;

said flowcell being configured to expose a segment of said core stream to said light beam;

a plurality of detectors, whereby individual detectors in said plurality of detectors are configured to receive a signal from a corresponding portion of said core stream, said signal resulting from an interaction of a particle in said corresponding portion of said core stream with said light beam;

a first plurality of sorting actuators connected with said flowcell, said first plurality of sorting actuators being positioned downstream of said segment of said core stream exposed to said light beam;

said first plurality of sorting actuators being in substantial alignment with the largest cross-sectional dimension of said core stream;

a plurality of sorting channels in fluid connection with said flow path and downstream of said first plurality of sorting actuators;

the sorting actuators of said first plurality of sorting actuators having multiple actuation states, each actuation state configured to direct at least one part of said core stream to a corresponding sorting channel of said plurality of sorting channels; and a second plurality of sorting actuators, said second plurality of sorting actuators being connected with said flowcell and opposite said first plurality of sorting actuators, actuators in said second plurality of sorting actuators being operable in coordination with actuators in said first plurality of sorting actuators.

A particle analyzer, comprising:

a source of a non-Gaussian, substantially nondiffracting light beam;

a flow path configured to produce a ribbon-like core stream in a flowcell, said core stream having a cross-sectional aspect ratio of at least 4 and a largest cross-sectional dimension of at least 50 micrometers;
said flowcell being configured to expose a segment of said core stream to said light beam; and
a plurality of detectors, whereby individual detectors in said plurality of detectors are configured to receive a signal from a corresponding portion of said core stream, said signal resulting from an interaction of a particle in said corresponding portion of said core stream with said light beam;
wherein said light beam is aligned with the largest cross-sectional dimension of said core stream under an angle of no more than 45 degrees.

A particle analyzer, comprising:
a source of a non-Gaussian, substantially nondiffracting light beam;
a flow path configured to produce a ribbon-like core stream in a flowcell, said core stream having a cross-sectional aspect ratio of at least 4 and a largest cross-sectional dimension of at least 50 micrometers;
said flowcell being configured to expose a segment of said core stream to said light beam; and
a plurality of detectors, whereby individual detectors in said plurality of detectors are configured to receive a signal from a corresponding portion of said core stream, said signal resulting from an interaction of a particle in said corresponding portion of said core stream with said light beam;
wherein said light beam is aligned substantially along the largest cross-sectional dimension of said core stream.

A particle analyzer, comprising:
a source of a light beam;
a flow path configured to produce a ribbon-like core stream in a flowcell, said core stream having a cross-sectional aspect ratio of at least 4 and a largest cross-sectional dimension of at least 50 micrometers;
said flowcell being configured to expose a segment of said core stream to said light beam; and
a plurality of detectors, whereby individual detectors in said plurality of detectors are configured to receive a signal from a corresponding portion of said core stream, said signal resulting from an interaction of a particle in said corresponding portion of said core stream with said light beam.

A particle analyzer, comprising:
a source of a light beam;
a flow path configured to produce a ribbon-like core stream in a flowcell, said core stream having a cross-sectional aspect ratio of at least 4 and a largest cross-sectional dimension of at least 50 micrometers;
said flowcell being configured to expose a segment of said core stream to said light beam;
a plurality of detectors, whereby individual detectors in said plurality of detectors are configured to receive a signal from a corresponding portion of said core stream, said signal resulting from an interaction of a particle in said corresponding portion of said core stream with said light beam;
a first plurality of sorting actuators connected with said flowcell, said plurality of sorting actuators being positioned downstream of said segment of said core stream exposed to said light beam;
said plurality of sorting actuators being in substantial alignment with the largest cross-sectional dimension of said core stream; and
a plurality of sorting channels in fluid connection with said flow path and downstream of said first plurality of sorting actuators;
the sorting actuators of said first plurality of sorting actuators having multiple actuation states, each actuation state configured to direct at least one part of said core stream to a corresponding sorting channel of said plurality of sorting channels.

A particle analyzer, comprising:
a source of a light beam;
a flow path configured to produce a ribbon-like core stream in a flowcell, said core stream having a cross-sectional aspect ratio of at least 4 and a largest cross-sectional dimension of at least 50 micrometers;
said flowcell being configured to expose a segment of said core stream to said light beam;
a plurality of detectors, whereby individual detectors in said plurality of detectors are configured to receive a signal from a corresponding portion of said core stream, said signal resulting from an interaction of a particle in said corresponding portion of said core stream with said light beam;
a first plurality of sorting actuators connected with said flowcell, said plurality of sorting actuators being positioned downstream of said segment of said core stream exposed to said light beam;
said plurality of sorting actuators being in substantial alignment with the largest cross-sectional dimension of said core stream;
a plurality of sorting channels in fluid connection with said flow path and downstream of said first plurality of sorting actuators;
the sorting actuators of said first plurality of sorting actuators having multiple actuation states, each actuation state configured to direct at least one part of said core stream to a corresponding sorting channel of said plurality of sorting channels; and
a second plurality of sorting actuators, said second plurality of sorting actuators being connected with said flowcell and opposite said first plurality of sorting actuators, actuators in said second plurality of sorting actuators being operable in coordination with actuators in said first plurality of sorting actuators.

A particle analyzer, comprising:
a source of a light beam;
a flow path configured to produce a ribbon-like core stream in a flowcell, said core stream having a cross-sectional aspect ratio of at least 4 and a largest cross-sectional dimension of at least 50 micrometers;
said flowcell being configured to expose a segment of said core stream to said light beam; and
a plurality of detectors, whereby individual detectors in said plurality of detectors are configured to receive a signal from a corresponding portion of said core stream, said signal resulting from an interaction of a particle in said corresponding portion of said core stream with said light beam;
wherein said light beam is aligned with the largest cross-sectional dimension of said core stream under an angle of no more than 45 degrees.

A particle analyzer, comprising:
a source of a light beam;
a flow path configured to produce a ribbon-like core stream in a flowcell, said core stream having a cross-sectional aspect ratio of at least 4 and a largest cross-sectional dimension of at least 50 micrometers;

said flowcell being configured to expose a segment of said core stream to said light beam; and a plurality of detectors, whereby individual detectors in said plurality of detectors are configured to receive a signal from a corresponding portion of said core stream, said signal resulting from an interaction of a particle in said corresponding portion of said core stream with said light beam;

wherein said light beam is aligned substantially along the largest cross-sectional dimension of said core stream.

DETAILED DESCRIPTION

Figure 1:
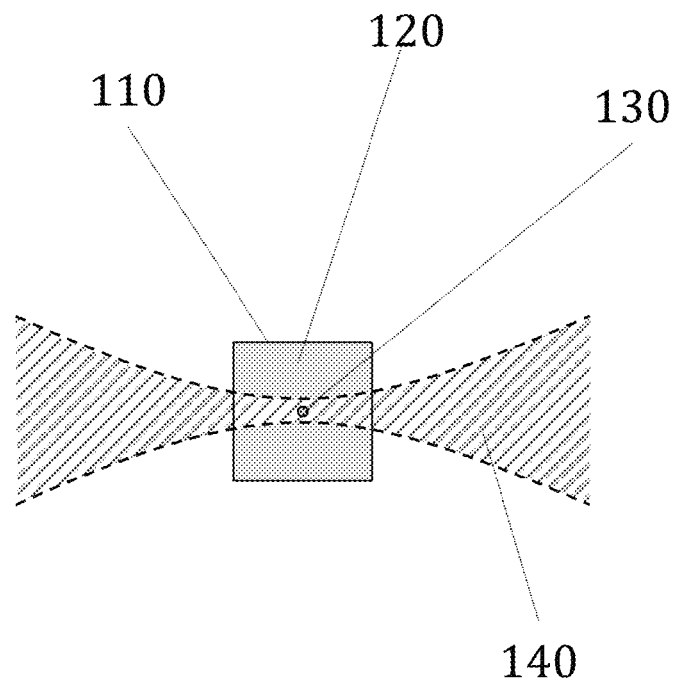
FIG. 1 is a schematic cross-sectional representation of the light-particle interaction region of a particle analyzer flowcell of the prior art.
Figure 1:
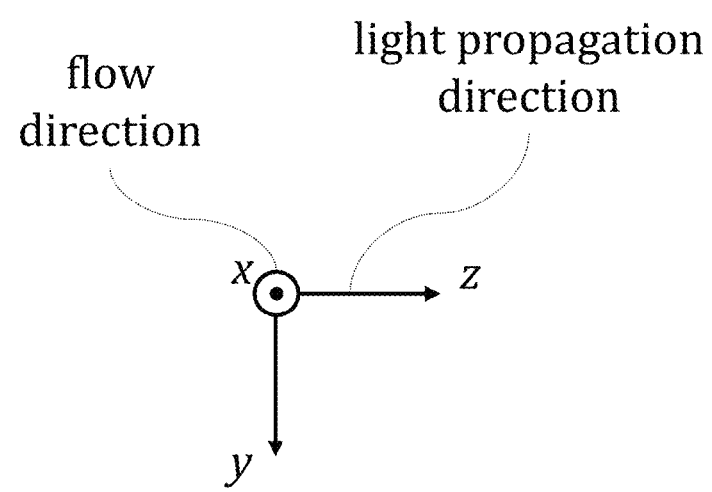

The invention pertains to the field of analysis of particles in a fluid stream. In some embodiments the particle analyzer is a Flow Cytometer. Specifically, embodiments of the invention are capable of increased flow throughput rates in particle analysis, in particular in Flow Cytometry. Some embodiments of the invention are capable of sorting of particles, in addition to their analytical capabilities.

Some embodiments of the present invention have the capability to deliver the desired extreme throughput by boosting a typical flow cytometer's volumetric analysis rate by a factor of at least 40; in some embodiments the increase may be up to a factor of more than 100. In some embodiments this is accomplished by eliminating one of the key constraints of current flow cytometer designs—a narrowly focused core stream, which has typically limited flow cytometry to volumetric analysis rates of no more than ~100 $\mu$L/min. By concentrating on rare-event applications, the typical requirement that cells must flow in single file is relaxed to allow for a much larger core-stream cross-section than normal. Some embodiments of the present invention are capable of analyzing one cell at a time just as in the current art, but the volume of fluid processed per unit time is multiplied dramatically, proportionately reducing analysis time.

Some embodiments of the invention may include capabilities to: (1) stretching the core stream out by a more than an order of magnitude in the direction of light propagation; (2) structuring the interrogating laser light beam to maintain near-diffraction-free propagation over the entire long dimension of the elongated core stream cross section. These capabilities are schematically illustrated in FIG. 2, in contrast to a typical implementation of flow cytometers of the prior art, shown in FIG. 1.

In order to achieve these capabilities, embodiments of the invention construct a light beam with a focused two-dimensional profile that propagates with minimal variation over a propagation length of from about 100 $\mu$m to 1000 $\mu$m or more. Further technical design elements may be included in embodiments of the invention.

Some embodiments comprise a flowcell geometry with a high aspect ratio to take advantage of hydrodynamic focusing and generate a stretched core stream. Such embodiments may leverage the high aspect ratio of a rectangular flowcell cross section to force the sample-bearing core stream, coming out of a standard circular nozzle, into a very thin ribbon surrounded by sheath fluid.

Some embodiments incorporate acoustic focusing to further or alternately coax the cells in the core stream to align tightly into a thin ribbon. The main shaping of the core stream may be carried out automatically by flowcell design and the properties of hydrodynamic focusing behavior; resonant acoustic focusing may confer to the thin core stream ribbon additional dynamic stability to ensure robust optical interrogation. Alternately, only acoustic focusing may be employed for the purpose of generating a ribbon-like core stream.

Additionally, embodiments of the invention may comprise design measures for the purpose of follow-on analysis of selected cells, and to avoid the relatively high forces associate with the impact with stationary liquid in traditional jet-in-air sorting.

Up until now, an assumption has existed that the geometry of a thin, wide core stream ribbon would cause unwanted differences in the light signals coming from cells at, say, opposite edges vs. the center of the ribbon itself. The following prophetic examples illustrate the expected benefits of the performance of the invention in this respect:

For instance, while a ribbon-like core stream is much elongated (in the forward direction of light propagation) as compared to a "pencil-like" core stream, even the extra-wide ribbon anticipated in this example confines the cells in the core stream to a small enough volume to render positional differences negligible in terms of forward scattering. The achieved geometry of a thin, wide core stream ribbon is not likely to cause unwanted differences in the light signals coming from cells at, say, opposite edges vs. the center of the ribbon itself. In particular, this example of an embodiment of the invention may produce a nominal 10° half-cone subtended by the collection pupil in the forward scattering geometry, about 30 mm away from the flowcell (typical for many types of analyzers). Cells not exactly in the center of the flowcell will give rise to a slightly wider or narrower cone of light collected by that same pupil, depending if they are closer or further away from it. In this example, based on the ribbon design long dimension of 480 µm, the range of cone half-angles goes from 9.92° to 10.07°. The effect that this variation causes on the amplitude of the scattering signal depends on many variables, such as particle size, composition, and wavelength of light used; a Mie scattering calculation based on a representative example results in Coefficients of Variation (CVs, equal to the standard deviation of a set of measurements divided by its mean) below 0.2%. Such values are very small compared to other instrumental contributions to measurement uncertainty, and essentially undetectable compared to natural cellular variability. In short, the minute additional uncertainty introduced will have no discernible effect on almost all applications.

Another concern that has existed until now refers to the potential impact of ribbon streaming on the side scattering and fluorescence signals. Specifically, from the point of view of fluorescence, the assumption has been that the proposed "extreme" ribbon streaming would cause signal variations because of (a) different power density of the excitation beam at different points in the ribbon, or (b) different dwell times of the cells in the light beam. These parameters have been engineered in embodiments of the present invention to overcome this issue: design choices, in terms of flowcell geometry, fluid injection rates, and beam profile, have been tailored to optimize performance according to multiple criteria. Specifically, point (a) may be managed, by design, through the use of a phase-structured, substantially nondiffracting beam, whose property is indeed to maintain a near-uniform cross-section over propagation lengths far longer than those of Gaussian beams, and sufficient to span the longitudinal width of the ribbon core stream. Point (b) may be managed, again by design, in several ways. For instance: first, by ensuring that the flowcell cross-sectional long dimension is sufficiently large to keep the core far enough from the flowcell walls and thus minimize viscous drag on the edges of the ribbon; and second, by optionally exploiting the transition region, in the most upstream section of the flowcell, where the fluid flow has not yet fully developed into a parabolic profile according to Poiseuille's Law. Together, these design elements may be used to keep cell velocity variations in the ribbon core to an acceptable minimum.

Another obstacle that has been raised in discussions of extended core streams is that of coincident (or doublet) events, namely when more than one cell is present in the illumination volume at the same time. The following prophetic example illustrates why this is not likely to be an issue with the present invention:

One can look at exemplary methods of performing assays in the invention, and in particular at dilution ratios of said methods, and estimate the average number of cells in the interrogation volume. Using some embodiments of the invention, a sample may be formed by either gently lysing the erythrocytes in whole blood (thereby effectively diluting the residual leukocytes with the erythrolytic reagent) or by presenting a cell suspension with concentrations comparable to that of leukocytes in a lysed preparation; for example, an approximate resulting concentration of 200 cell/µL is typical in both cases (platelets and erythrocyte debris will be small enough to be easily discriminated by appropriate trigger settings on the detection channels). The interrogation volume in an exemplary embodiment of the invention may be around 145 pL; this yields an average occupation number of around 0.029 cells (meaning that, on average, each cell is separated from another by about 35 interrogation volumes). Even accounting for Poisson statistics, the predicted coincidence rate for such concentrations is exceedingly low. Indeed, cell concentrations could be much higher than assumed here without resulting in any significant coincidence-related issues.

It is important to note that the assumed dilution ratio (about 1:20 for whole blood) is entirely consistent with the extreme-throughput analysis rates typical of embodiments of the invention. By coupling the substantially nondiffracting Bessel beam edge-on with an extremely wide but thin core stream, embodiments of the invention may be capable of operating a particle analyzer, such as a flow cytometer, with a volumetric sample throughput of over 4,000 µL/minute—a value about 40 times that of current flow cytometers. At the projected core flow rate of approximately 4,300 µL/min, an entire 7.5-mL tube of peripheral whole blood, diluted 1:20 in an erythrolytic reagent, may be analyzed in 35 minutes: a dramatic improvement over the state of the art. Some embodiments of the invention may be capable of flows of about 10,000 µL/minute, or about 100 times the typical volumetric throughput of current flow cytometers. The higher volumetric throughput of some embodiments may be achieved by generation of a ribbon-like sample core stream with a longer cross-sectional major axis, optionally with a longer minor cross-sectional axis, and with an interrogating light beam with substantially nondiffracting behavior over a correspondingly longer distance to encompass the longer propagation through the long cross-sectional dimension of the core stream.

Table 1 illustrates selected design and performance aspects of exemplary and preferred embodiments of the invention.

TABLE 1

| Design Feature | Exemplary Embodiments | Preferred embodiments |
| --- | --- | --- |
| core stream thickness (across light propagation) | 5-100 μm | >20 μm |
| core stream width (along light propagation) | 50-5,000 μm | >400 μm |
| core stream cross-section | 250-500,000 μm$^2$ | >8,000 μm$^2$ |
| core stream aspect ratio | 4-200 | >20 |
| core stream flow speed | 0.1-50 m/s | >1 m/s |

Figure 2:
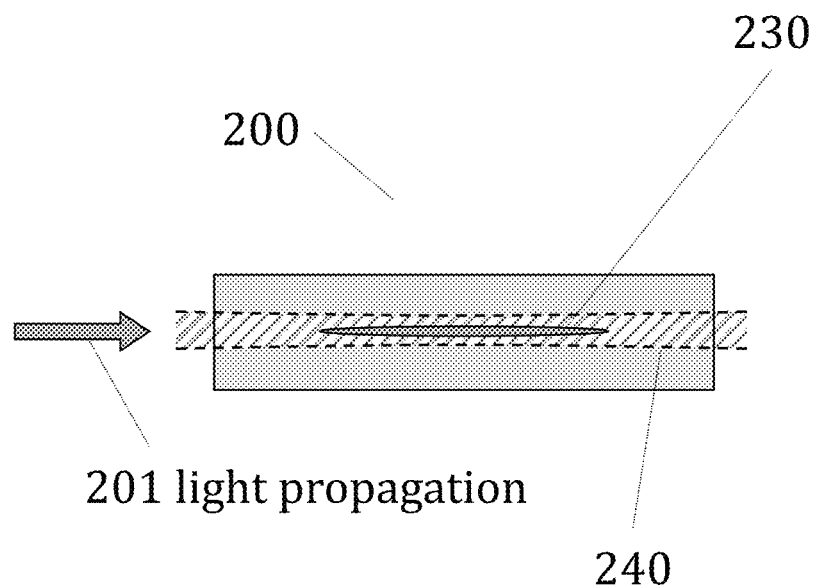
FIG. 2 is a schematic cross-sectional representation of the light-particle interaction region of a particle analyzer/sorter flowcell with a substantially nondiffracting light beam and an extended core stream.
Figure 2:
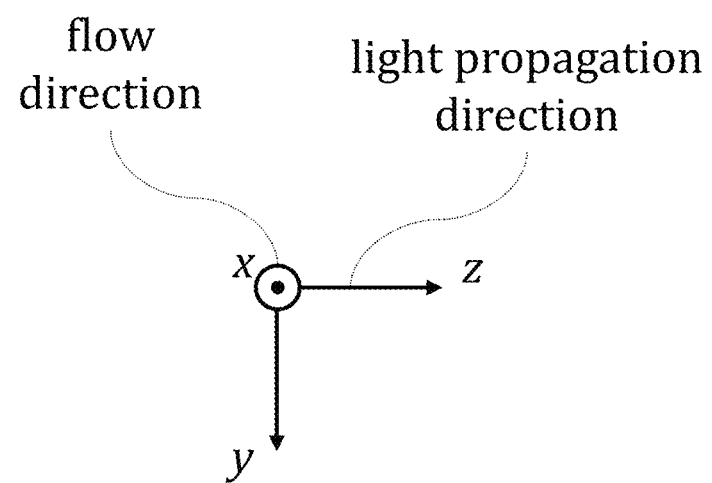

FIG. 1 illustrates a cross-section, perpendicular to the direction of fluid flow, of a typical region of interaction between light and a particle to be analyzed in a flowcell of the prior art. Internal surface 110 of a flow cell is schematically indicated in the figure, and provides a channel for fluid flow. Sheath fluid 120 is provided to confine a fluid carrying particles to be analyzed. The sheath fluid and the particle-carrying fluid are focused into a flowcell lumen, usually by hydrodynamic means, alternatively by acoustic focusing, channel microstructuring, deterministic lateral displacement, dielectrophoresis, or other particle-focusing means; such focusing produces a tight sample core stream 130 bounded by the sheath fluid. Both the sheath fluid and the sample core stream flow in a direction x perpendicular to the plane of the page and toward the viewer. An interrogating Gaussian beam 140 with customary diffracting behavior is provided to interact with the particles in the sample core stream 130. The light beam 140 propagates in a direction z substantially perpendicular to the flow direction. The beam 140, usually having a Gaussian intensity profile, is generally focused into a relatively tight spot in the plane of the sample core stream 130. Due to the nature of light waves and the principles of diffraction, a tight beam spot is produced by a strongly converging input beam and results into a strongly diverging output beam. As a consequence, the longitudinal range over which the beam spot is approximately uniform and tight (a range related to an optical quantity known in the art as the Rayleigh range) is relatively small. The beam is generally focused in both directions perpendicular to the direction of light propagation z, namely along the x axis and the y axis As illustrated in FIG. 2, some embodiments of the invention are capable of generating a core stream, elongated in the direction of light propagation, in a particle analyzer. FIG. 2 illustrates a cross-section, perpendicular to the direction of fluid flow, of the region of interaction between light and a particle to be analyzed in an embodiment of a flowcell of the current invention. Compared to the prior art illustrated in FIG. 1, a flowcell 200 is significantly elongated in the direction of light propagation 201; a sample core stream 230 is tight only in the transverse direction y perpendicular to light propagation, and extended in the direction z parallel to it; and an interrogating light beam 240 is provided having a non-Gaussian nature, designed to produce an extended Rayleigh range. The propagation direction 201 of light beam 240 is substantially aligned with the major cross-sectional axis (the z dimension in FIG. 2) of the extended sample core stream. In some embodiments of the invention, the light propagation direction makes an angle of between 0 and 45 degrees with the major cross-sectional axis of the extended sample core stream to more directly expose particles in the sample core stream to the interrogating light.

In flow cytometers of the prior art, the variation of local light intensity over the illuminated portion of the sample core stream due to diffraction effects (i.e., convergence of the beam into and divergence out of the beam waist plane) is generally on the order of less than 1% for typical core stream dimensions (around 10-20 μm) and beam waist dimensions (referring to FIG. 1, about 10-25 μm in the x flow direction and about 50-100 μm in the transversal y direction). Variations in light intensity due to the shape of the beam profile are generally on the order of 1 to 5%, and it is generally accepted that signal variations due to the interaction between the interrogating light beam and the core stream should be kept to less than about 5% to provide useful overall system results. In a flow cytometer of the prior art employing traditional beams with customary diffraction properties, the maximum longitudinal (referring to FIG. 1, z direction) core stream size compatible with these requirements is around 150 μm. The extended Rayleigh range of the non-Gaussian beam of the current invention may achieve variations in light intensity below about 1% while allowing longitudinal (referring to FIG. 2, z direction) core stream dimensions of 400 μm or more; and it may achieve variations below about 5% with longitudinal core stream dimensions of 1000 μm or more. Herein, beams having this property are referred to as "substantially nondiffracting" beams.

One example of a substantially nondiffracting beam having preferable propagation characteristics to those of a Gaussian beam is a type of beam known in the art as a Bessel beam. One preferable feature of such beams is their ability to maintain an approximately uniform beam spot size over longer ranges than is the case with normally diffracting Gaussian beams of comparable intensity, wavelength, and minimum beam spot waist. This extended range, or extended depth of focus, makes it possible to interrogate particles in a sample core stream extended in the longitudinal direction z. Such extended sample core stream 230 is referred to as ribbon-like on account of its much greater extent longitudinally (along the direction of light propagation z) than transversally (across the direction of light propagation, along direction y). The flowcell dimensions are designed in such a way as to generate, e.g. through hydrodynamic focusing, a sample core stream with the desired dimensions and cross-sectional aspect ratio. The core stream dimensions are alterable by control of sample core stream injection pressure or flow rate, by control of sheath injection pressure or flow rate, and by control of the relationship between the two. Additionally, a degree of control can be exerted in terms of the location, along the flowcell microchannel, where the laser beam intersects the sample core stream, to take advantage of the hydrodynamic formation region where the flow profiles have not yet converged onto a translationally-invariant form.

Figure 3:
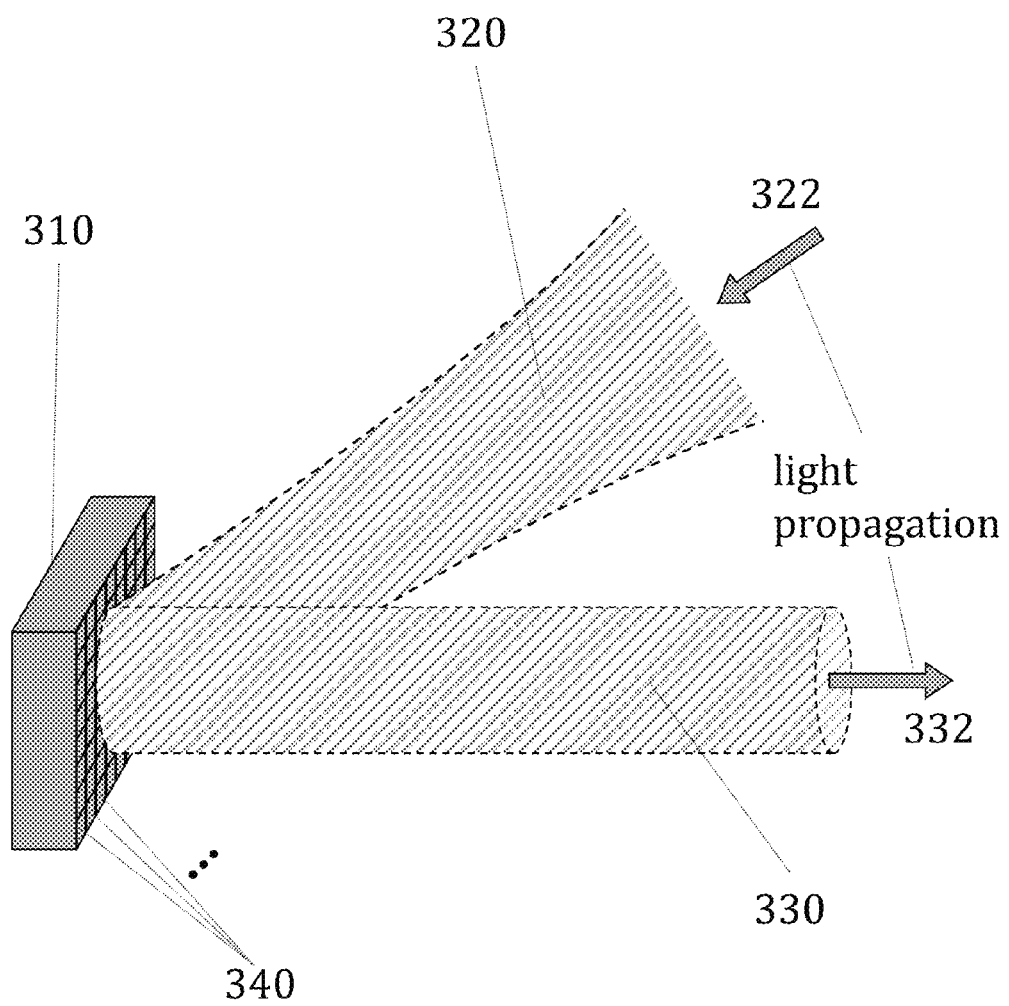
FIG. 3 is a schematic representation of a reflective Spatial Light Modulator used to dynamically modify the phase and/or intensity profile of an incoming light beam and produce a substantially nondiffracting outgoing beam.

FIG. 3 illustrates one possible embodiment of an optical device used to produce a non-Gaussian beam in the present invention. A device 310 referred to in the art as a Spatial Light Modulator (SLM) is provided to interact by reflection with an ordinary input beam 320 having a Gaussian intensity distribution traveling along incoming propagation direction 322, and produce a non-Gaussian output beam 330 having substantially nondiffracting intensity and phase profiles traveling along outgoing propagation direction 332. The interaction by reflection is effected by a plurality of elements 340 of the SLM, each of which is addressable individually by electronic means to impart upon the portion of the input beam that strikes it a desired amount of phase shift. The input beam is sized so as to overlap a number of individual SLM elements. The larger the ratio between the area of the impinging input beam and the area of individual SLM elements, the finer the resolution and the control on the propagation characteristics of the output beam. The individual SLM elements are programmed electronically to impart mathematically defined phase shifts to the portions of the beam that impinge upon each one, and result in an output beam having substantially nondiffracting propagation characteristics, with a beam waist having an atypically long range of approximate uniformity. The location, downstream from the SLM, where the output beam acquires and maintains substantially nondiffracting waist characteristics, is designed to overlap with the location of the ribbon-like sample core stream in the flowcell. An example of a reflective-type SLM is one where each individually addressable element 340 is a micromirror. Another, preferred example of a reflective-type SLM is one where each individually addressable element 340 is a pixel in a two-dimensional liquid-crystal array with a reflective backplane, each such pixel imparting a variable, desired phase shift on the portion of the wavefront that impinges on it upon propagation through the liquid crystal to the reflective backplane and back out. To program SLM 310 to deliver the desired beam characteristics, one possible procedure starts with defining the desired beam profile and divergence behavior at a certain surface (e.g., the point of interrogation in the middle of the sample core stream), mathematically or computationally backpropagating the wavefronts to the surface of the SLM upstream in an optical model of the system based on descriptions, standard in the art, of the light waves in terms of Maxwell's equations or functionally equivalent treatments, and thereby deriving the requirements for the SLM configuration necessary to then produce the desired effect in the actual forward-propagating implementation. Such calculations are periodically refreshed by a processing unit on the basis of feedback from sensors onboard the instrument, or on the basis of projected changes in the optical or physical parameters of the system over factors including, for instance, time, environmental conditions, and the refractive index of materials.

Figure 4:
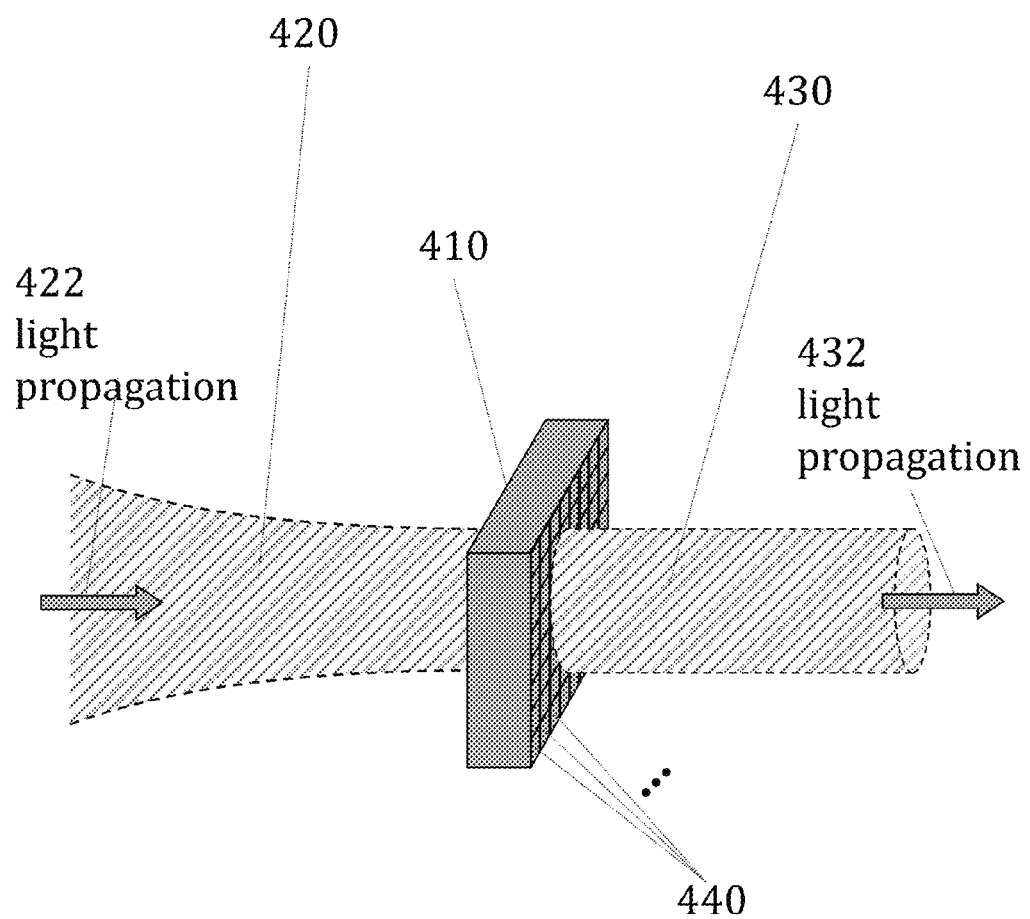
FIG. 4 is a schematic representation of a transmissive Spatial Light Modulator used to dynamically modify the phase and/or intensity profile of an incoming light beam and produce a substantially nondiffracting outgoing beam.

FIG. 4 illustrates another possible embodiment of an optical device 410 used to produce a substantially nondiffracting beam 430 in the present invention. It is similar in concept to the device illustrated in FIG. 3 except that its interaction with the input beam 420 is by transmission rather than by reflection. An example of a transmissive-type SLM is one where each of the individually addressable elements 440 is a transmission-type liquid-crystal pixel, arranged in a two-dimensional array. The incoming Gaussian beam 420 travels along incoming propagation direction 422, experiences a phase shift programmable by pixel location in SLM 410, and travels out along outgoing propagation direction 432 as a non-Gaussian, substantially nondiffracting beam 430. The process used to determine the phase and/or intensity transformations needed from each pixel 440 is similar to the one used to compute the analogous transformations for optical device 310, one difference being that the transformations in the case of device 410 are experienced during transmission rather than during reflection as in the case of device 310.

Figure 5:
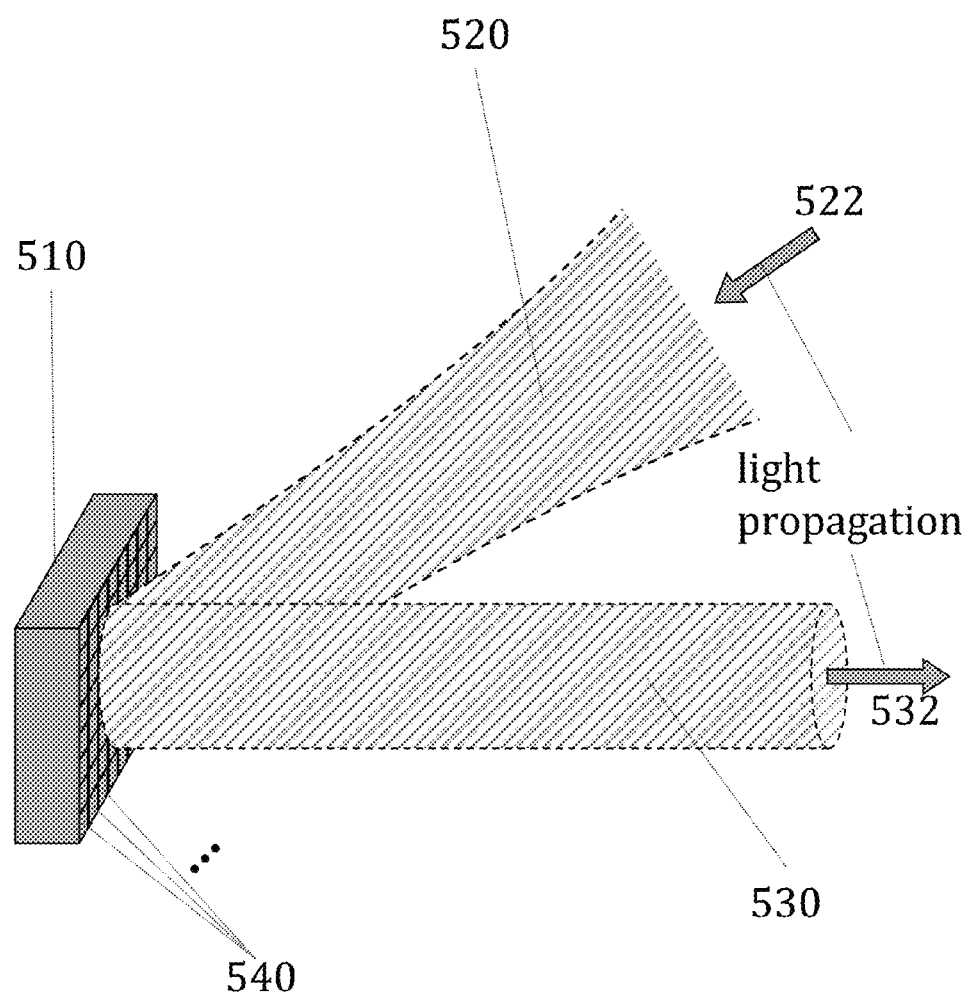
FIG. 5 is a schematic representation of a reflective phase/intensity mask used to modify the phase and/or intensity profile of an incoming light beam in a fixed way and produce a substantially nondiffracting outgoing beam.

FIG. 5 illustrates another possible embodiment of an optical device 510 used to produce a substantially nondiffracting beam 530 in the present invention. It is similar in concept to the device illustrated in FIG. 3 except that instead of comprising means of dynamically changing the configuration of the individually addressable elements, it provides a phase/intensity mask 510 comprising a set of permanent, static phase- and/or intensity-control elements 540 predesigned to achieve a desired effect upon the impinging input beam 520. The incoming Gaussian beam 520 travels along incoming propagation direction 522, experiences a phase shift dependent on pixel location in mask 510, and travels out along outgoing propagation direction 532 as a non-Gaussian, substantially nondiffracting beam 530. An example of a reflective-type phase/intensity mask is one where each predesigned phase-/intensity-control element 540 is a microcolumn having a variably mirrored, optionally variably oriented top facet and a height from baseline computed to result in the desired phase shift and intensity modulation upon the impinging input beam. Means of producing such a permanent phase/intensity mask, a "static SLM," include etching a silicon surface with the desired topographical characteristics (extent, elevation over baseline, surface orientation, and degree of reflectivity of individual wavefront control elements) and using such surface as a master to produce molds out of inexpensive material, such as, e.g., polymers, through a process such as injection molding. In the case of a reflective-type static SLM, the polymer molds would then be coated with a thin conformal layer of reflective material such as metal (e.g., aluminum, silver, or gold, depending on the required reflectivity and the design wavelength range) to produce a two-dimensional array of static micromirrors. In accordance with common practice in master/mold processing, the master silicon surface is etched in such a way that the molds acquire the desired topography of micromirror elements—in other words, the etching program produces a silicon surface complementary to the one ultimately desired. Alternative means of producing a reflective-type static SLM include, for instance, hot embossing, micropatterning, microimprinting, micromachining, and additive manufacturing techniques such as 3-D manufacturing, laser sintering, and two-photon polymerization. The process used to determine the phase and/or intensity transformations needed from each phase-/intensity-control element (pixel) 540 is similar to the one used to compute the analogous transformations for optical device 310, one difference being that the properties in the case of device 510 are fixed and therefore are calculated to address the most likely or common operating conditions encountered by the apparatus.

Figure 6:
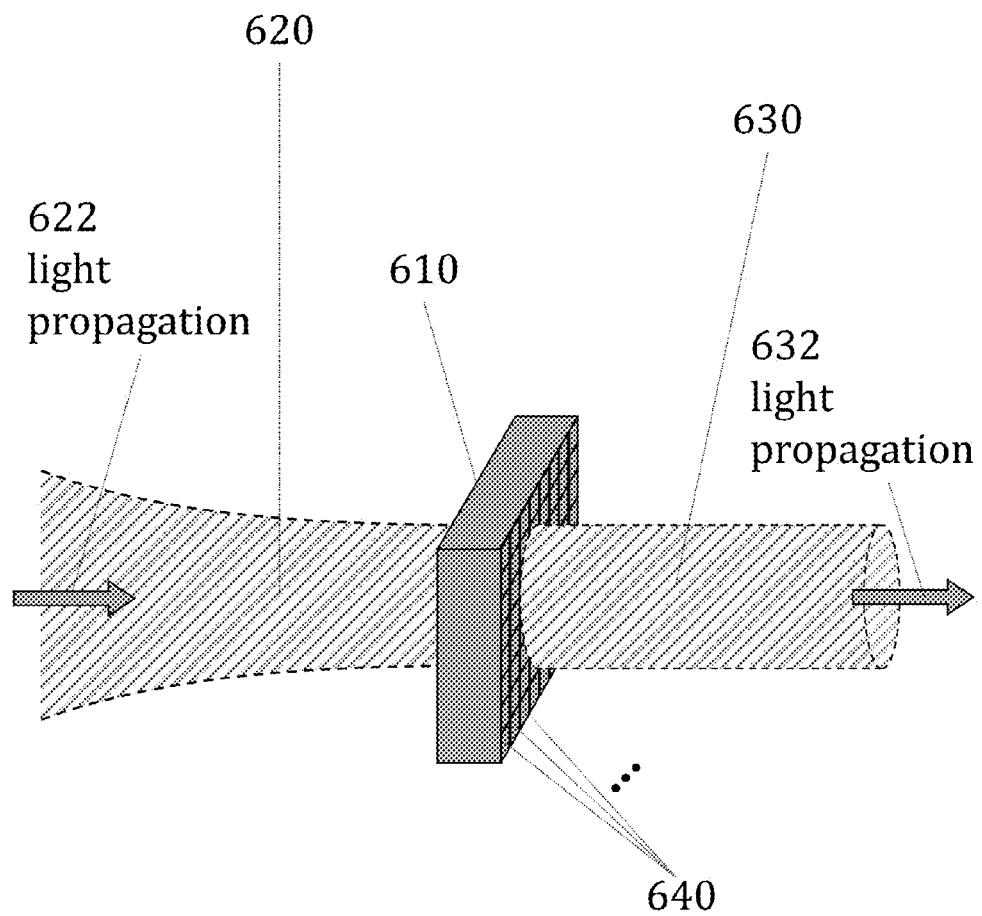
FIG. 6 is a schematic representation of a transmissive phase/intensity mask used to modify the phase and/or intensity profile of an incoming light beam in a fixed way and produce a substantially nondiffracting outgoing beam.

FIG. 6 illustrates another possible embodiment of an optical device 610 used to produce a substantially nondiffracting beam 630 in the present invention. It is similar in concept to the device illustrated in FIG. 5 except that its interaction with the input beam 620 is by transmission rather than by reflection. The incoming Gaussian beam 620 travels along incoming propagation direction 622, experiences a phase shift dependent on pixel location in mask 610, and travels out along outgoing propagation direction 632 as a non-Gaussian, substantially nondiffracting beam 630. An example of a transmissive-type phase/intensity mask is one where each of the predesigned phase-/intensity-control elements 640 is a transparent microcolumn having a height from baseline computed to result in the desired phase shift and intensity modulation upon the impinging input beam. Manufacture of a transmissive-type static SLM may be realized by similar means to those described for the reflective-type static SLM in reference to FIG. 5, except that the intermediate component (examples of which include, for instance, polymer molds or laser-sintered glass) is not coated with a metal layer, but may optionally be coated with antireflection layers optionally variable on a pixel-by-pixel basis. The process used to determine the phase and/or intensity transformations needed from each phase-/intensity-control element (pixel) 640 is similar to the one used to compute the analogous transformations for optical device 410, one difference being that the properties in the case of device 610 are fixed and therefore are calculated to address the most likely or common operating conditions encountered by the apparatus.

Figure 7:
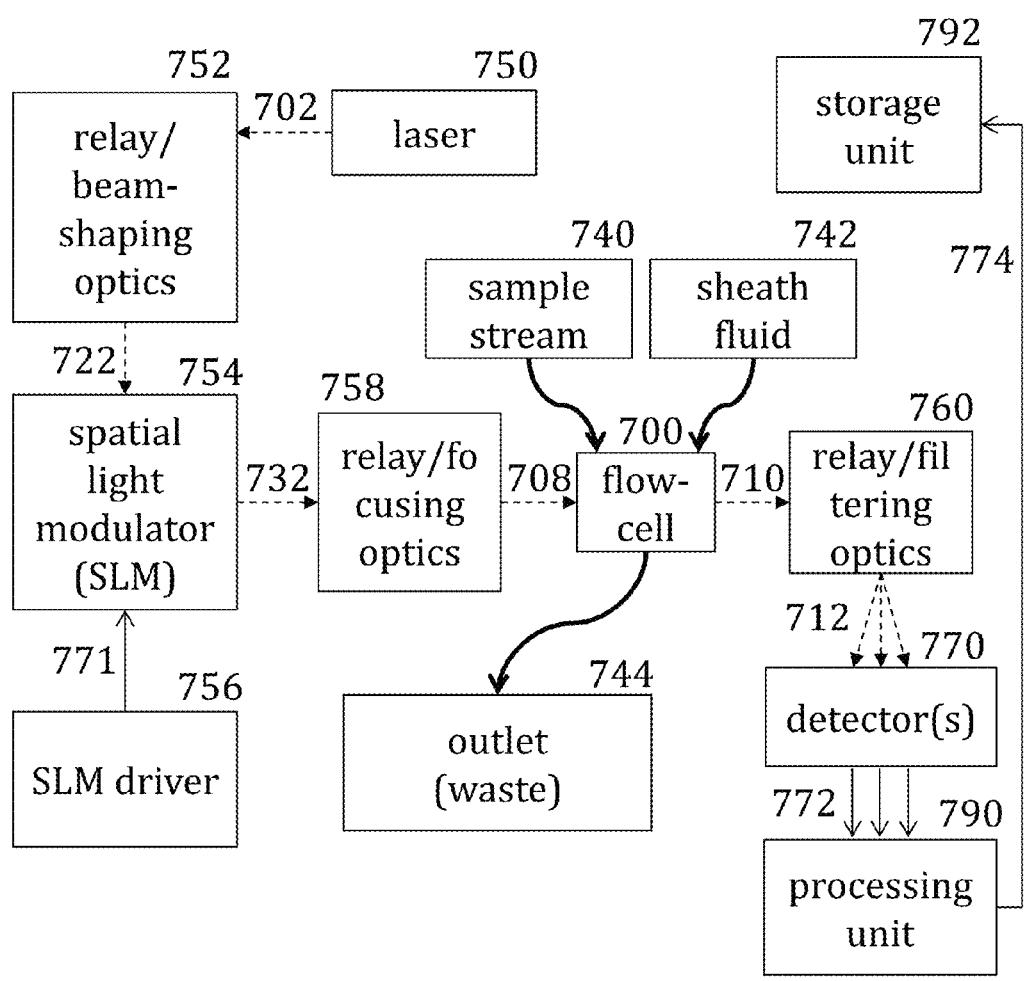
FIG. 7 is a schematic illustration of a system configuration of an apparatus for high-throughput analysis of single particles in a sample.

FIG. 7 illustrates schematically a system configuration of an exemplary embodiment of the present invention, which provides an apparatus for high-throughput analysis of single particles in a sample. A light source 750, e.g., a laser, produces a beam 702 with desired wavelength, power, and dimensions. The beam is directed by means of relay optics 752 (which can include, for instance, lenses, mirrors, prisms, or optical fibers) as beam 722 to a spatial light modulator (SLM) 754. In the context of this application, relay optics will be intended to represent means to transmit a beam from one point in the system to another, and will also be intended to represent means to shape a beam in terms of dimensions and convergence, divergence or collimation. In the context of this application, SLM will be taken to mean both reflective- and transmissive-type SLMs, and will also be taken to mean dynamic SLMs as well as static phase/intensity masks. SLM 754 may be any one of optical devices 310, 410, 510, 610, from Figs., respectively, 3, 4, 5, or 6, or any other suitable optical device designed to achieve a substantially similar phase and/or intensity transformation. In the case of a dynamic SLM, an SLM driver 756 provides the instructions 771 necessary to produce in the SLM 754 the configuration of individually addressable elements to result in the desired output beam propagation characteristics. The output beam 732 from the SLM is directed to another set of relay optics 758 (which can include, for instance, lenses, mirrors, prisms, or optical fibers), which may additionally optionally perform a focusing function. This second set of relay optics then directs the beam 708 to the flowcell 700. The flowcell 700 provides for the passage of particles to be analyzed (which can include, for instance, cells, bacteria, exosomes, liposomes, microvesicles, microparticles, nanoparticles, and natural or synthetic microspheres) by conveying a sample stream 740 containing said particles and a stream of sheath fluid 742 that surrounds and confines said sample stream, as described above in reference to FIG. 2. An input portion of the flowcell focuses, e.g., by hydrodynamic means, the sample stream and the surrounding sheath stream to result in a tight sample core stream flowing through a microchannel portion of the flowcell, surrounded by sheath fluid. The sheath fluid and the sample core stream are directed to a single outlet 744 (and generally discarded as waste) after passage through the interrogation portion of the flowcell. The cross-section of the microchannel portion of the flowcell has an aspect ratio whereby the dimension perpendicular to the propagation of the interrogating light beam (direction y in FIG. 2) is much smaller than the dimension parallel to the propagation of the interrogating light beam (direction z in FIG. 2). The aspect ratio of the flowcell cross-section is chosen to result in the sample core stream having a tight dimension generally perpendicular to the light beam and an extended dimension generally aligned with the light beam. As the interrogating light beam interacts with particles in the sample core stream by scattering, absorption, fluorescence, and other means, light signals 710 are generated. These light signals are collected by relay optics in box 760 (which can include, for instance, single lenses, doublet lenses, multi-lens elements, mirrors, prisms, optical fibers, or waveguides) positioned around the flowcell, then conveyed to filtering optics in box 760 (which can include, for instance, colored filters, dichroic filters, dichroic beamsplitters, bandpass filters, longpass filters, shortpass filters, multiband filters, diffraction gratings, prisms, or holographic optical elements) and then conveyed as filtered light signals 712 by further relay optics in box 760 to one or more detectors 770 (which can include, for instance, photodiodes, avalanche photodiodes, photomultiplier tubes, silicon photomultipliers, or avalanche photodiode microcell arrays). The detectors convert the light signals 712 into electronic signals 772, which are optionally further amplified and groomed to reduce the impact of unwanted noise. The electronic signals are sent to an electronic processing unit 790 (which can include, for instance, a standalone computer, a single-board computer, a microprocessor, a field-programmable gate array, a digital signal processing board, or a combination of two or more of these), which executes further processing steps upon the electronic signals. The processed signals 774 are then sent to a data storage unit 792 (which can include, for instance, a read-only memory unit, a flash memory unit, a hard-disk drive, an optical storage unit, an external storage unit, or a remote or virtual storage unit connected to the instrument by means of a wired data network, a Wi-Fi link, an infrared communication link, or a cellular telephony network link). The stored or preliminarily processed data, or both, can also be made available to an operator for optional inspection of results.

Figure 8:
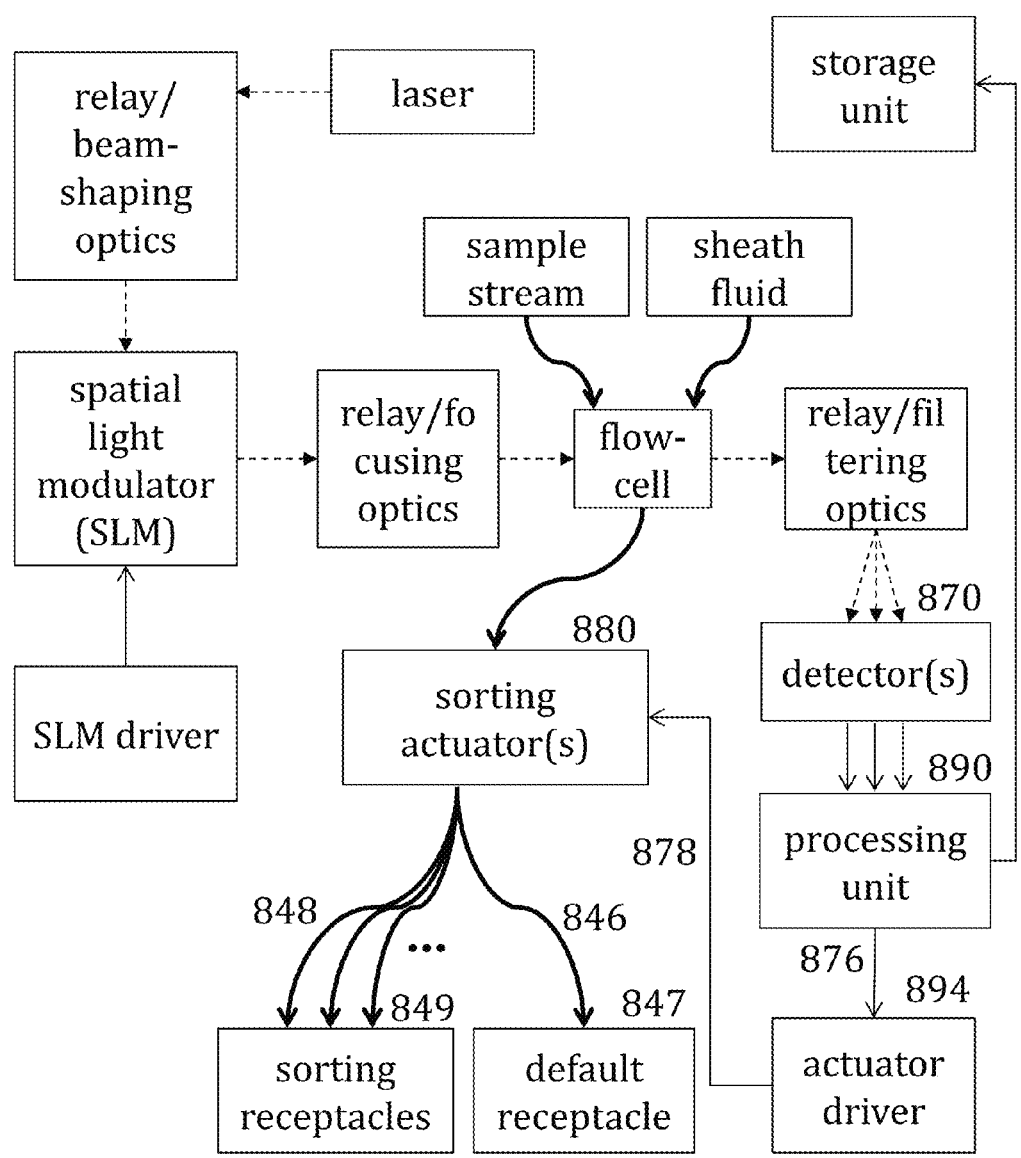
FIG. 8 is a schematic illustration of a system configuration of an apparatus for high-throughput analysis and sorting of single particles in a sample.

FIG. 8 illustrates schematically a system configuration of an exemplary embodiment of the present invention, which provides an apparatus for high-throughput analysis and sorting of single particles in a sample. It is similar in configuration to the system configuration of FIG. 7, except in that it additionally provides for the capability to sort and collect particles based on their characteristics. The electronic processing unit 890 generates in real time sorting control signals 876 based on the presence or absence or degree or nature of predetermined characteristics of the particles to be analyzed. For example, it may be desirable to identify and sort particles that, upon excitation by the interrogating light beam, emit fluorescence in a predefined spectral band at a level above a predefined threshold. The processing unit, once the processed signals from each particle meet the predefined set of sorting criteria, triggers a signal 876 conveyed to an actuator driver 894. The actuator driver is an electronic control module connected to one or more sorting actuators 880. The sorting actuators may be positioned in, on, next to, or near the flowcell in the vicinity of, and downstream from, the interrogation region. One or more of the sorting actuators 880 is temporarily activated by drive signal 878 from the actuator driver 894 in response to the triggering signal 876 from the processing unit 890, resulting in a temporary diversion of the sample core stream, or of a portion of the sample core stream, away from the default sorting channel 846 and into one or more sorting channels 848. The default sorting channel 846 optionally directs the fluids it receives into a default receptacle 847. The sorting channels 848 direct the selected portions of the sample core stream to one or more receiving sorting receptacles 849. Following the temporary activation of one or more of the sorting actuators 880, the actuator(s) return to their resting state, and the sample core stream returns to its default sorting channel 846. The sorting actuators 880 are controllable to achieve multiple actuation states, for instance, with an actuator driver 894, with a built-in control, with direct voltage or current control from the processing unit 890, or with electrical signals coming directly from logic circuitry connected with the one or more detectors 870.

Figure 9:
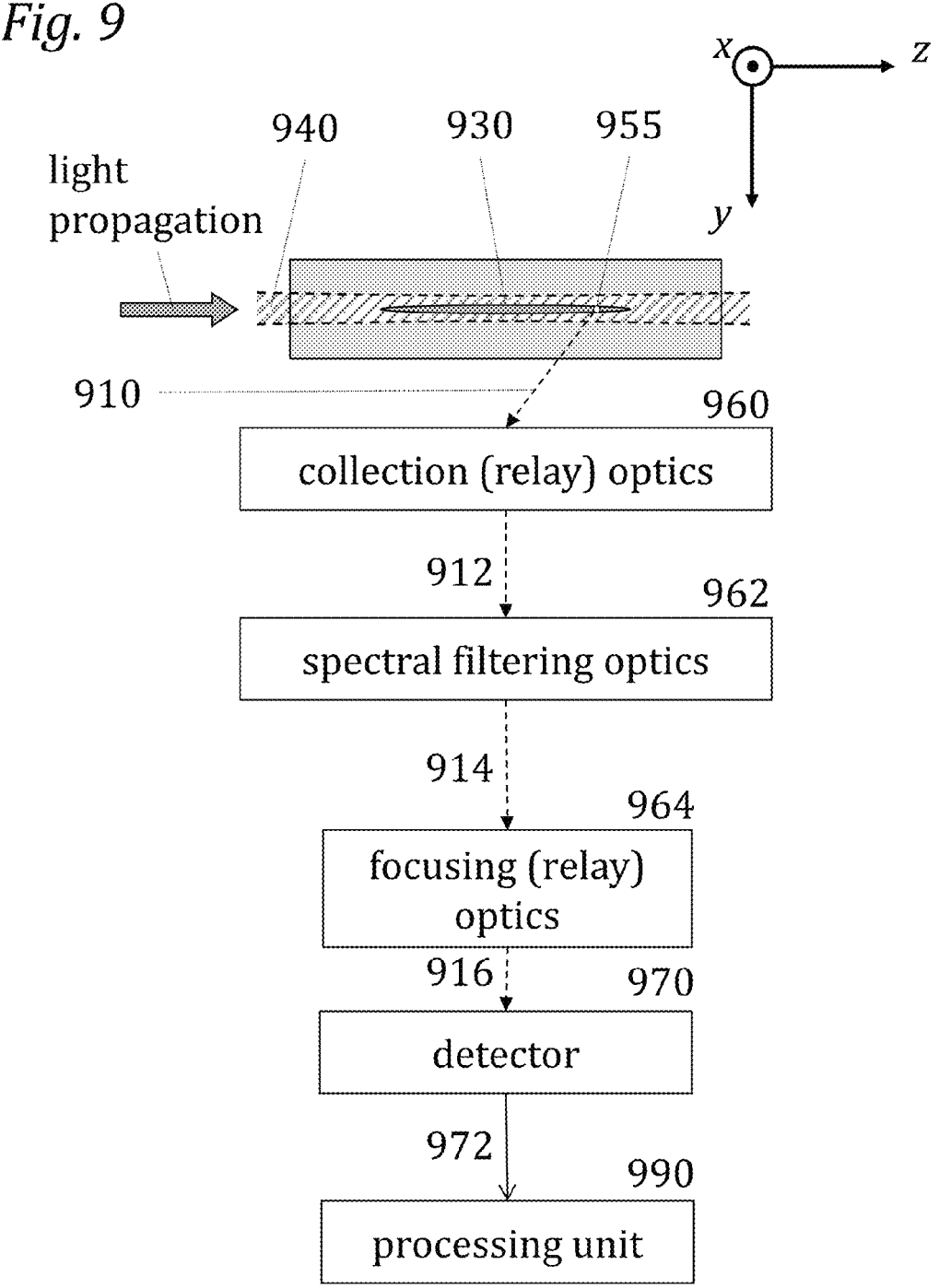
FIG. 9 is a schematic representation of the light collection and detection subsystem of a high-throughput particle analyzer/sorter with a single spectral detection band.
Figure 10:
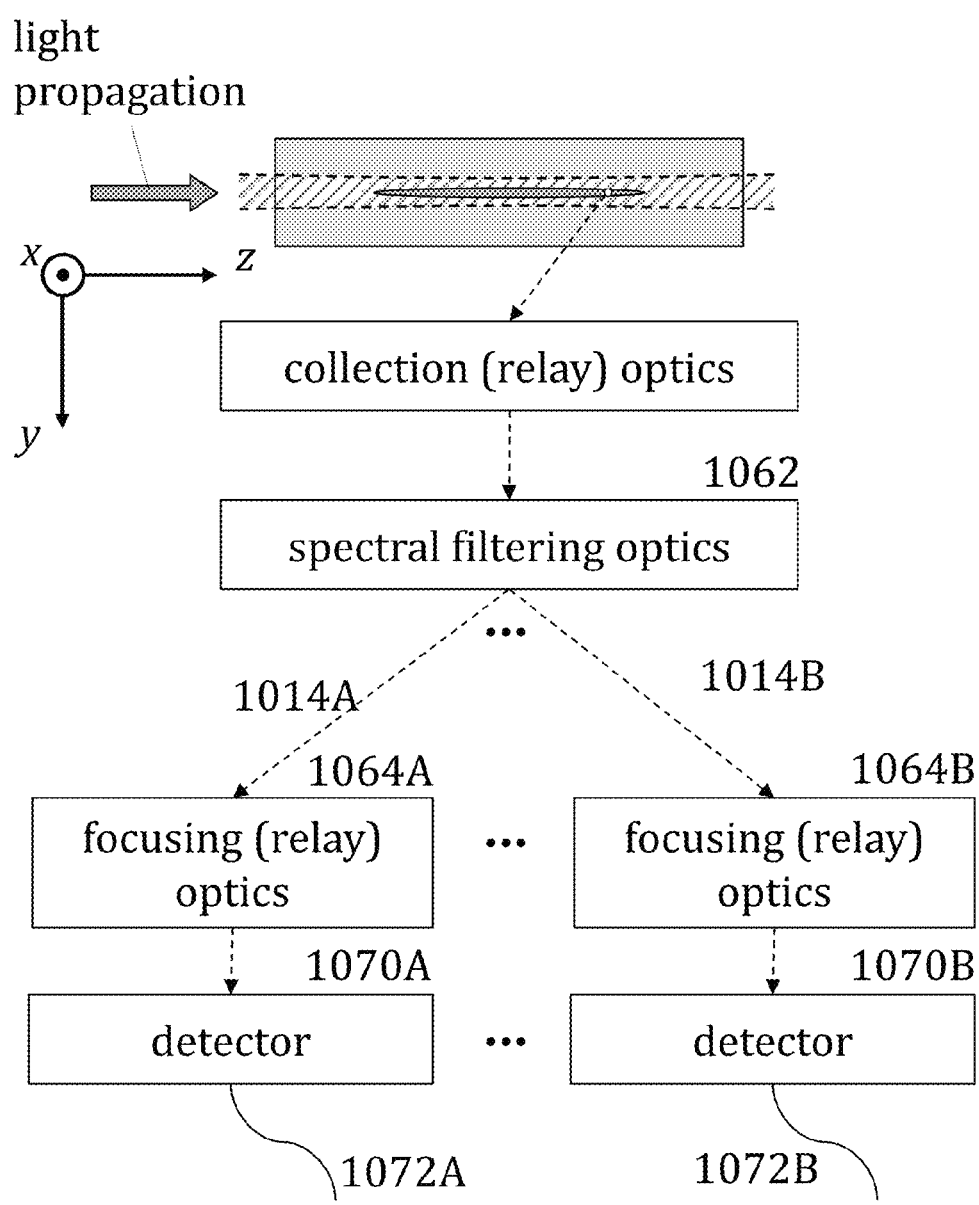
FIG. 10 is a schematic representation of the light collection and detection subsystem of a high-throughput particle analyzer/sorter with multiple spectral detection bands.
Figure 11:
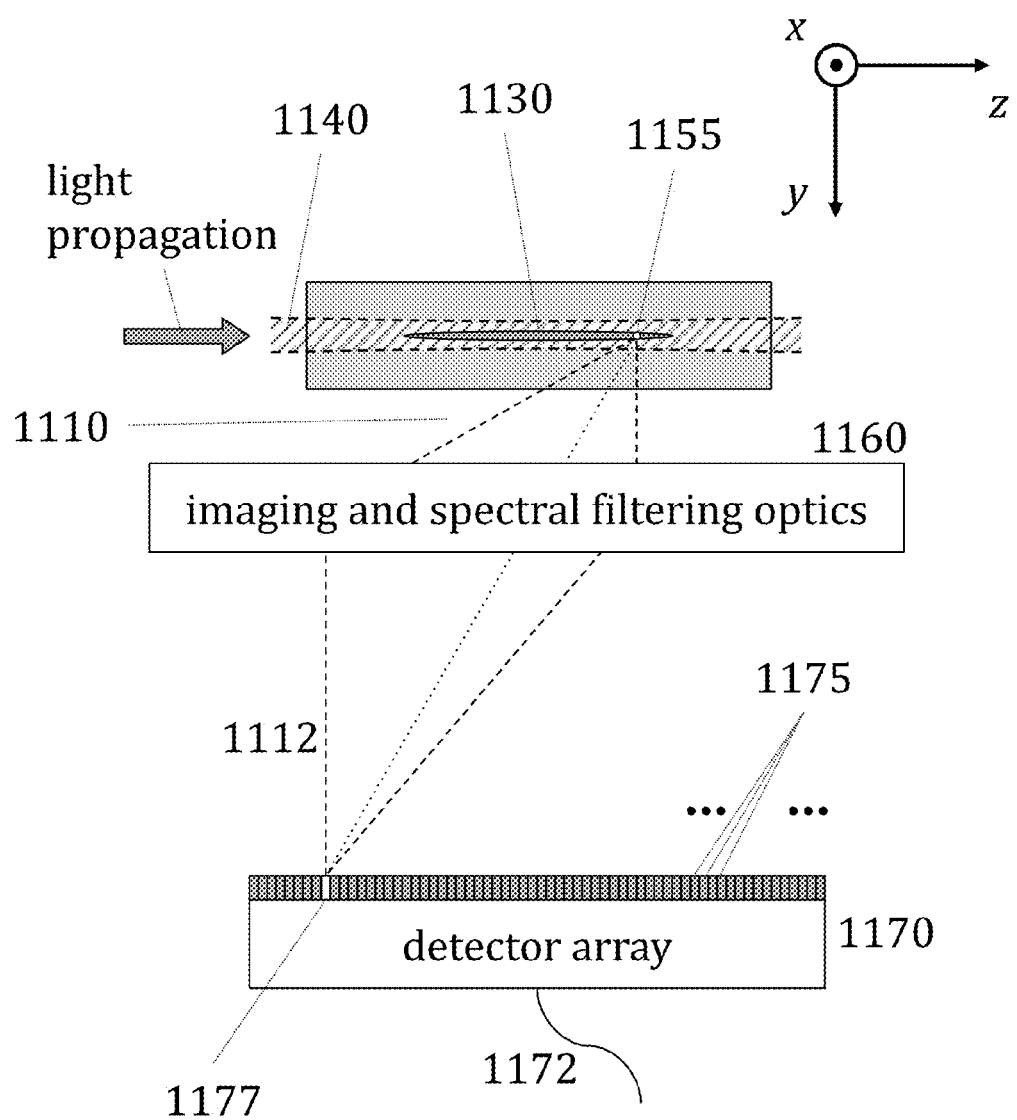
FIG. 11 is a schematic representation of the light collection and detection subsystem of a high-throughput particle analyzer/sorter with a position-resolving detector array.

In FIGS. 9, 10, and 11, the relative orientation of fluid flow, light propagation, and transverse directions is shown, respectively, as the set of axes x, z, and y, similarly to the depiction in FIG. 2.

FIG. 9 illustrates a cross-section, perpendicular to the direction of fluid flow, of a possible light collection configuration of the present invention. The ribbon-like sample core stream 930 in a flowcell is illuminated by the interrogating substantially nondiffracting beam 940. Particles (of which a representative particle 955 is shown, at one of the many possible locations within the cross section of the sample core stream) to be analyzed in the sample core stream interact with light in the beam 940 to generate light signals 910 by optical processes including, for instance, scattering, absorption, or fluorescence. The light signals 910 are collected by collection optics 960. The collected light signals 912 are then conveyed to spectral filtering optics 962 to select appropriate spectral bands of the light signals for detection. The spectral filtering optics 962 may be, for instance, reflective, transmissive, absorptive, diffractive, or holographic in nature or based on interference, or a combination thereof. The resulting spectrally filtered light signals 914 are then conveyed as signals 916 by focusing optics 964 to a detector 970. The detector converts the light signals 916 into electrical signals 972, which are then conveyed to a processing unit 990 for further analysis, processing, and optionally storage, as described above in reference to FIGS. 7 and 8. Together, the collection optics 960 and the focusing optics 964 may be referred to as relay optics.

In some embodiments, more than one spectral band output may be generated. For instance, FIG. 10 illustrates a cross-section, perpendicular to the direction of fluid flow, of another possible light collection configuration of the present invention. It is similar in concept to the configuration illustrated in FIG. 9 except that the spectral filtering optics 1062 produce more than one spectral band output 1014 (A and B), separated according to spectral characteristics. Each spectral band is then conveyed to a separate set of focusing optics 1064 (A and B) and separate detectors 1070 (A and B), resulting in respectively separate electrically converted signals 1072 (A and B). FIG. 10 depicts, for the sake of clarity, two sets of spectral bands, focusing optics, and detectors; it will be apparent to those skilled in the art that an arbitrary number of such sets is encompassed by the scope of the invention.

FIG. 11 illustrates a cross-section, perpendicular to the direction of fluid flow, of yet another possible light collection configuration of the present invention. It provides for a similar set of collection, spectral filtering, and focusing functions as described for FIG. 9, and in addition it also preserves the spatial location information of the particles 1155 in the ribbon-like sample core stream 1130. The optical layout of this configuration is referred to in the art as an imaging layout. An image of the portion of the sample core stream 1130 illuminated by the interrogating substantially nondiffracting beam 1140 is formed by imaging and spectral filtering optics 1160 (which can include, for instance, single lenses, doublet lenses, multi-lens elements, mirrors, prisms, optical fibers, or waveguides) onto the detector array 1170. An example of imaging optics is a set of two positive (e.g., planoconvex, biconvex, best-form, aspherical, or compound achromatic doublet or other multi-element) lenses, each placed at distances corresponding to their respective effective focal lengths, the first (closest to the flowcell) its focal length away from the x-z plane of the ribbon-like sample core stream, the second (closest to the detector array) its focal length away from the x-z plane of the active surface of the detector array, some distance interposed in between the two. Spectral filtering optics may be inserted in the space between the two lenses. The light rays 1110 from a single particle 1155 are collected, passed through imaging and spectral filtering optics 1160 as described above in relationship to FIG. 9, and relayed onto the detector array 1170. The detector array may be, for instance, a linear array of detector elements 1175 or a two-dimensional array of detector elements 1175. The dimension of the detector array corresponding to the long dimension of the sample core stream cross-section (i.e., that along direction z) is designed to image the sample core stream so that a monotonic, 1:1 mapping relationship is created between positions of particles like particle 1155 within the sample core stream 1130 along direction z and positions along said dimension of the detector array. The light signals from a single particle being analyzed may result in a single element or in multiple elements 1177 of the detector array being illuminated. It is not necessary for a conventional digital image (i.e., consisting of multiple pixels in a two-dimensional array) of any of the particles like particle 1155 to be formed onto detector array 1170; the nature of the imaging optics 1160 referred herein is characterized by the relatively faithful, relatively undistorted reproduction, whether magnified, minified, or unchanged in size, of objects on the object plane (i.e., the illuminated portion of the sample core stream) as images on the conjugate image plane (i.e., the detector array). This faithful reproduction is referred to in the art as an "image" whether or not any given particle under analysis is detected by more than one element of the detector array (thereby forming a traditional, multi-pixel image) or by just a single element of the detector array. The detector array 1170 converts the light signal information 1112 impinging upon one or more of its illuminated elements 1177 into electronic signals 1172 conveyed to a processing unit for further analysis, processing, and optionally storage, as described above in reference to FIGS. 7 and 8.

The plurality of detectors in the embodiment disclosed above is described in a preferred embodiment as an array. It should be understood than any suitable plurality of detectors may be used for the purpose as indicated, whether configured as an array or otherwise.

Whereas preferred embodiments of the invention comprise a plurality of detectors, embodiments with a single detector are included under the scope of the invention. Their construction may be entirely analogous to any single one of the plurality of detectors.

Figure 12:
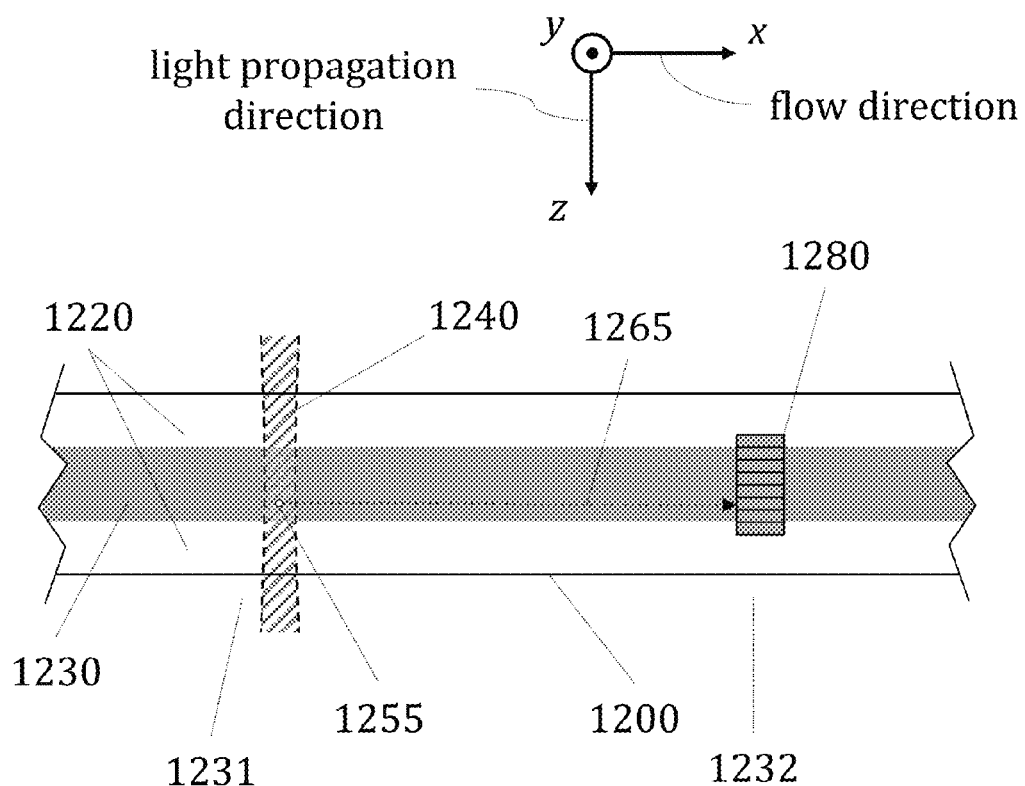
FIGS. 12(a) and (b) are schematic plan-view illustrations of two steps, or states, of a high-throughput particle analysis/sorting method that uses an actuator array.
Figure 12:
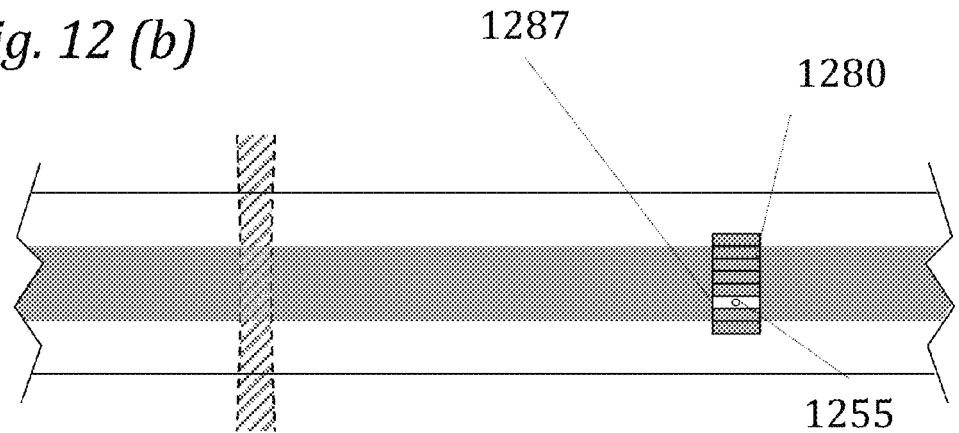

FIGS. 12(a) and 12(b) illustrate exemplary embodiments of two steps of a high-throughput analysis and sorting method of the current invention. In FIGS. 12(a) and 12(b), the relative orientation of fluid flow, light propagation, and transverse directions is shown as the set of axes x, z, and y, respectively. The assignment of the axes and directions is similar to that in FIG. 2, however the orientation of the axes with respect to the page is rotated as compared to FIG. 2, with the light propagation and flow directions being in the plane of the page in FIGS. 12(a) and (b). Each of the two figures shows a schematic representation of a side view of the interrogation region 1231 and sorting region 1232 of the flowcell 1200. The focusing region of the flowcell, if provided, e.g., by hydrodynamic means, is to the left of the picture; the ribbon-like sample core stream 1230, surrounded by the sheath fluid 1220, comes in from the left and flows towards the right. The sheath fluid 1220 is bounded by the inner walls of the flowcell 1200, and the sample core stream 1230 is bounded by the sheath fluid 1220. In the interrogation region 1231 at left, the substantially nondiffracting beam 1240 is delivered to the flowcell by external optics and intersects the sample core stream 1230. In the sorting region 1232 at right, one or more actuators (shown in the picture as an actuator array 1280) are provided in contact with or near the flowcell, positioned in such a way as to overlay the position of the sample core stream 1230.

FIG. 12(a) shows a first time step in the processing of a sample whereby a single particle 1255 in the sample core stream 1230 enters the interrogation region 1231 (where the beam 1240 intersects the sample core stream 1230). The light-particle interaction generates light signals as described above in reference to FIG. 11, which light signals are collected and relayed to a detector array. Based on the design of the imaging optical layout, the detector array registers the position, across the ribbon-like sample core stream 1230 along direction z, of the particle 1255, and conveys that information to a processing unit as illustrated schematically in FIG. 8. As described above in reference to FIG. 8, the processing unit uses that information to produce a triggering signal for an actuator driver, which driver in turn activates an element of the actuator array 1280 in FIG. 12(a). FIG. 12(b) shows a second time step in the processing of the sample whereby the particle 1255 detected in the step depicted in FIG. 12(a), after following path 1265 in the flowcell along direction x, arrives at a point in the vicinity of the actuator array 1280 in the sorting region 1232 of the flowcell. The design of the imaging optical layout and of the detection, processing, and control electronics is such that the actuator element 1287 that is activated is the element calculated, estimated, predicted or found upon calibration or determined empirically during instrument design or assembly to be nearest to a passing particle following a similar path. The timing of the triggering signal (i.e., the relative delay from particle detection to sorting actuation) is designed to take into account both the average velocity of fluid flow in the flowcell and its spatial profile across the flowcell cross-section, according to the characteristics of Poiseuille flow known in the art and as modified based on empirical or modeling information. The triggering delays for each of the actuator elements 1287 are likewise calculated, calibrated or determined.

The plurality of actuators in the embodiment disclosed above is described in a preferred embodiment as an array. It should be understood than any suitable plurality of actuators may be used for the purpose as indicated, whether configured as an array or otherwise.

Whereas preferred embodiments of the invention comprise a plurality of actuators, embodiments with a single actuator are included under the scope of the invention. Their construction may be entirely analogous to any single one of the plurality of actuators.

Figure 13:
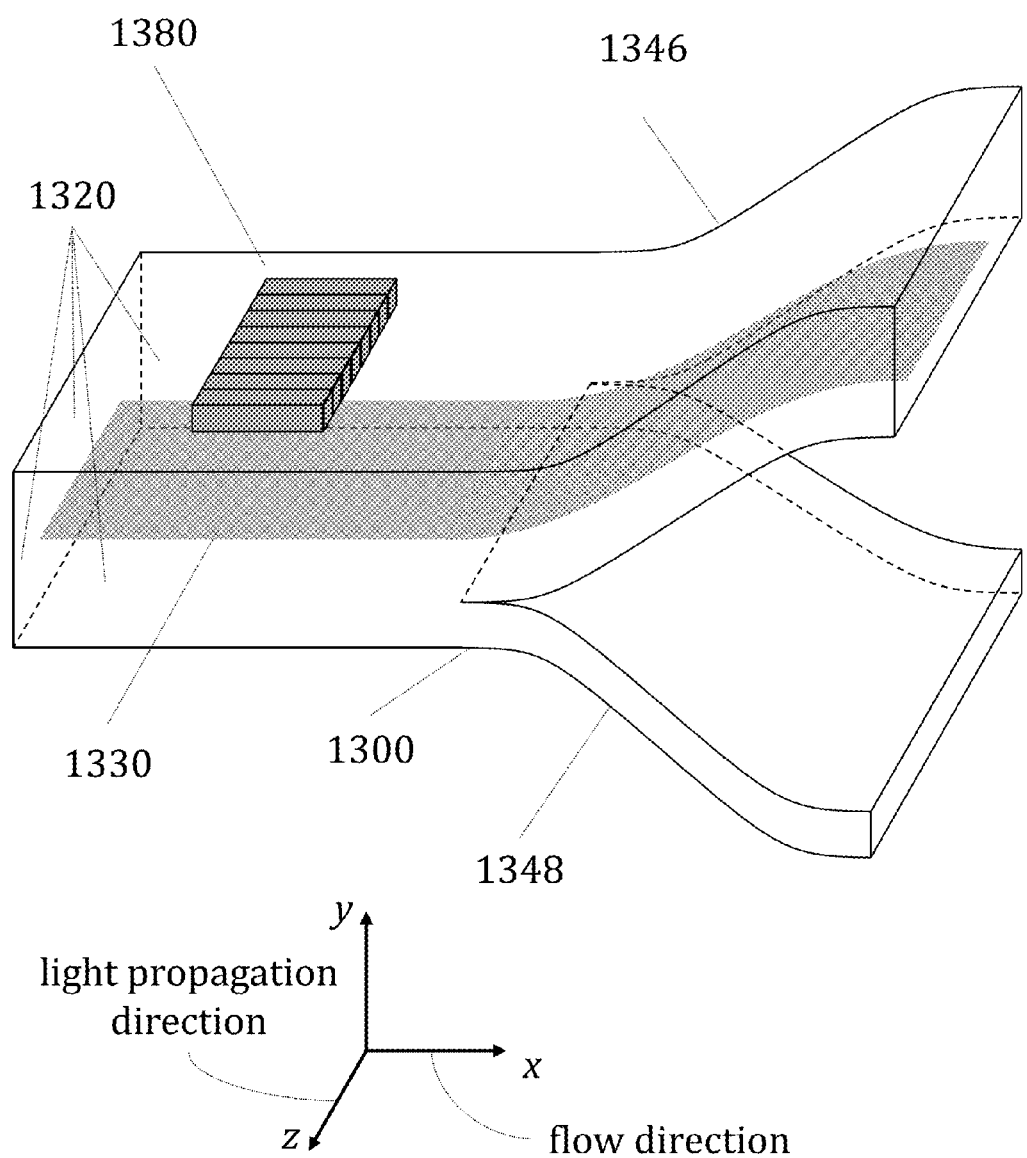
FIGS. 13(a) and (b) are schematic isometric illustrations of two steps, or states, of a high-throughput particle analysis/sorting method that uses an actuator array.
Figure 13:
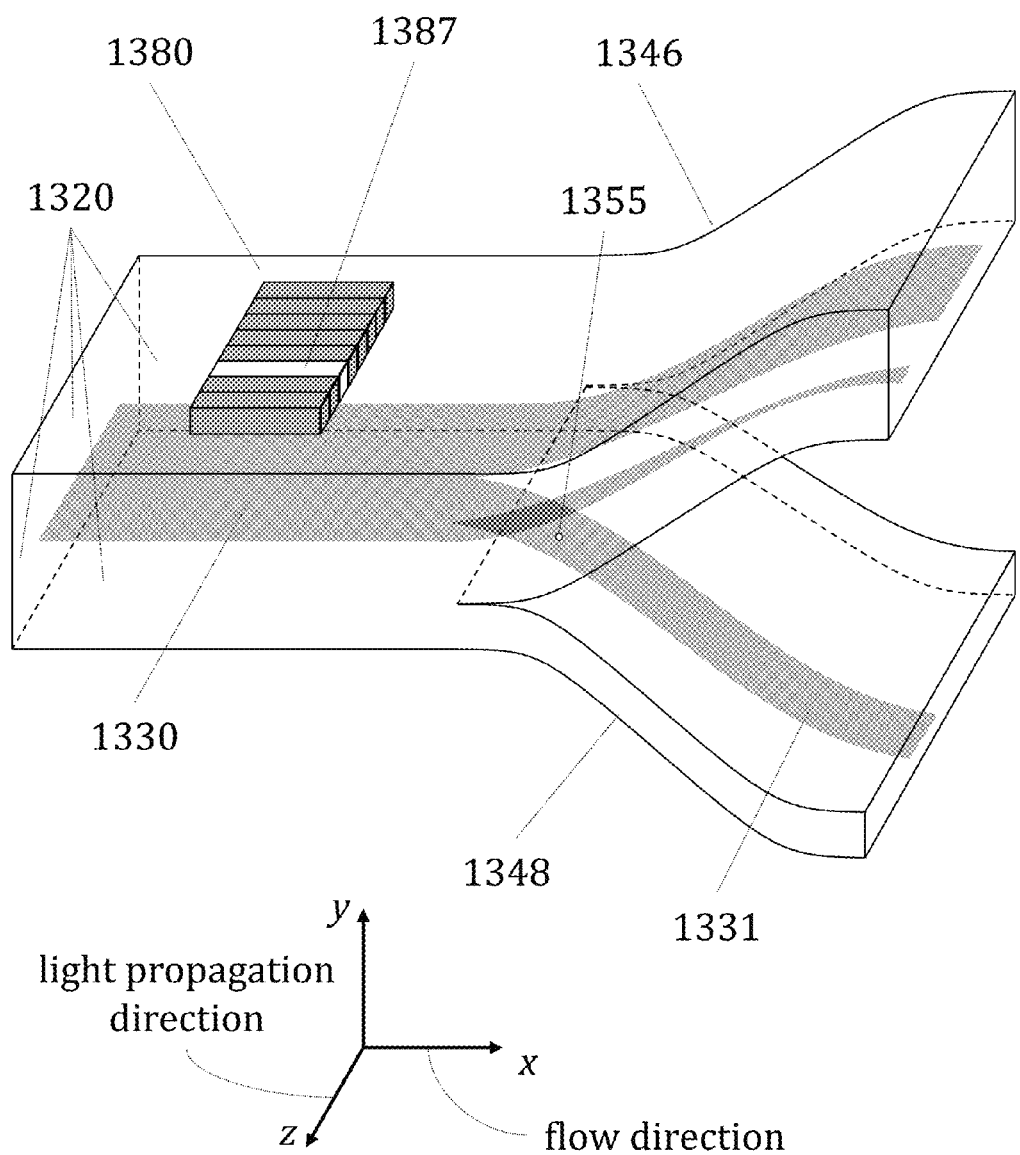
Figure 17:
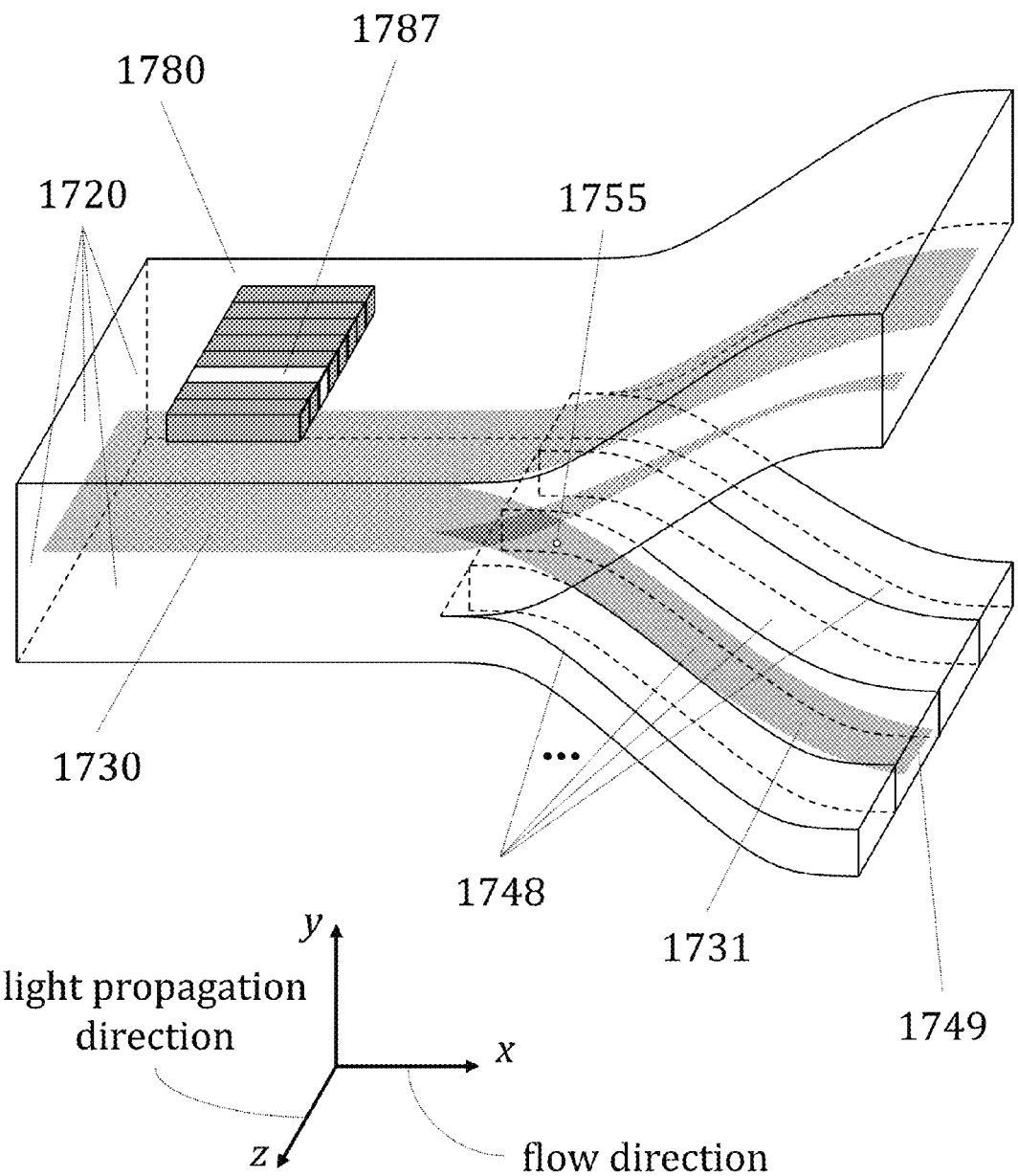
FIG. 17 is a schematic isometric illustration of one step, or state, of a high-throughput particle analysis/sorting method that uses an actuator array and multiple sorting channels.

In FIGS. 13(a), 13(b), and 17, the relative orientation of fluid flow, light propagation, and transverse directions is shown as the set of axes x, z, and y, respectively. The assignment of the axes and directions is similar to that in FIG. 2, however the orientation of the axes with respect to the page is rotated as compared to FIG. 2, with the fluid flow and transverse directions being in the plane of the page in FIGS. 13(a), 13(b), and 17.

FIG. 13(a) is a schematic isometric depiction of the sorting region of the flowcell in a default state of one representative embodiment of the current invention. The focusing region of the flowcell, e.g., by hydrodynamic means, if provided, is to the left of the picture; the ribbon-like sample core stream 1330, surrounded by the sheath fluid 1320, comes in from the left and flows towards the right. The flowcell 1300 splits into two channels in the sorting region: the default sorting channel 1346 and the sorting channel 1348. The actuator array 1380 is depicted as embodied in, in contact with, or in proximity of the inner wall of the flowcell on the default sorting channel side. In this illustration of the default state, all the actuator elements are in the OFF state, resulting in the entire sample core stream 1330 flowing by design into the default sorting channel 1346.

FIG. 13(b) is a schematic isometric depiction of the sorting region of the flowcell in an exemplary sorting state of one representative embodiment of the current invention. The elements depicted common to FIG. 13(a) are as described above in reference to FIG. 13(a). In this illustration of an exemplary sorting state, one of the actuator elements 1387 in the array 1380 is activated, while the rest are in the OFF state. Selection of the actuator element (or elements) for activation is based on the prior detection step using a detector array, as described above in reference to FIGS. 11 and 12(a) and 12(b). Activation of the indicated actuator element 1387 results in the diversion into the sorting channel 1348 of the sorted portion 1331 of the sample core stream closest to the activated element, which portion contains a desired particle 1355 detected upstream and automatically selected by analysis algorithms to trigger sorting actuation, while the rest of the sample core stream 1330 continues to flow undiverted into the default sorting channel 1346.

In FIGS. 14(a) and (b), 15(a) and (b), 16(a) and (b), and 18(a)-(d), the relative orientation of fluid flow, light propagation, and transverse directions is shown as the set of axes x, z, and y, respectively. The assignment of the axes and directions is similar to that in FIG. 2, however the orientation of the axes with respect to the page is rotated as compared to FIG. 2, with the fluid flow and transverse directions being in the plane of the page in FIGS. 14(a) and (b), 15(a) and (b), 16(a) and (b), and 18(a)-(d). The cross-sectional plane depicted in FIGS. 14(a) and 14(b), 15(a) and (b), 16(a) and (b), and 18(a)-(d) is the plane that contains the particle being analyzed and sorted.

Figure 14:
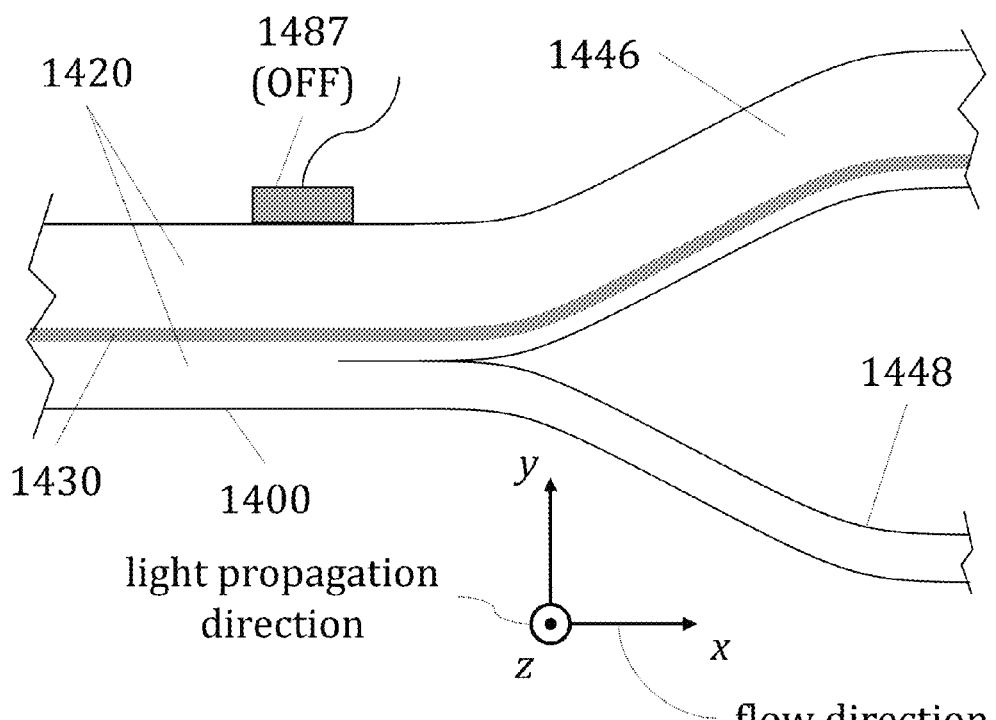
FIGS. 14(a) and (b) are schematic cross-sectional illustrations of two steps, or states, of a high-throughput particle analysis/sorting method with two sorting states and one-sided actuation.
Figure 14:
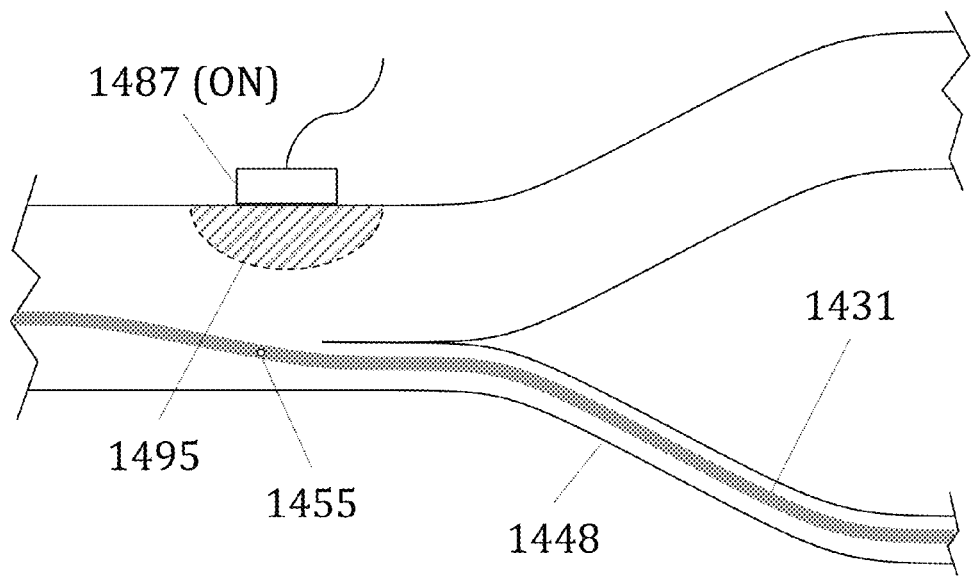

FIGS. 14(a) and 14(b) illustrate one embodiment of two states of the high-throughput sorting method of the current invention. Each of the two figures shows a schematic representation of a cross-sectional view of the sorting region of the flowcell. Similarly to the situation depicted in FIGS. 13(a) and (b), the focusing region of the flowcell, e.g., by hydrodynamic means, if provided, is to the left of the picture; the ribbon-like sample core stream 1430, surrounded by the sheath fluid 1420, comes in from the left and flows towards the right. The flowcell 1400 splits into two channels in the sorting region: the default sorting channel 1446 and the sorting channel 1448. An element 1487 of the actuator array is depicted as embodied in, in contact with, or in proximity of the inner wall of the flowcell 1400 on the default sorting channel side. Similarly to the state depicted in FIG. 13(a), FIG. 14(a) shows the configuration of the default state, where with the actuator element 1487 in the OFF state, the portion of the sample core stream 1430 shown in this cross-sectional view flows by design into the default sorting channel 1446. Similarly to the state depicted in FIG. 13(b), FIG. 14(b) shows the configuration of the sorting state, where with the actuator element 1487 in the ON state, a transient gas, vapor, or gas-vapor bubble, or a region of heated or cooled, less-dense sheath fluid 1495 is generated (by means including, for instance, thermal means, electrolytic means, and gas injection means), which creates a localized flow diversion in the depicted cross-sectional plane and in its immediate vicinity, which diversion deflects the portion 1431 of the sample core stream shown in this cross-sectional view into the sorting channel 1448, which portion contains a particle 1455 detected upstream and automatically selected by analysis algorithms to trigger sorting actuation. Following deactivation of the depicted actuator element 1487, the transient gas, vapor, gas-vapor bubble or region of less-dense fluid 1495 shrinks or is cleared away, and the flow pattern returns to the original default state of FIG. 14(*a*).

Figure 15:
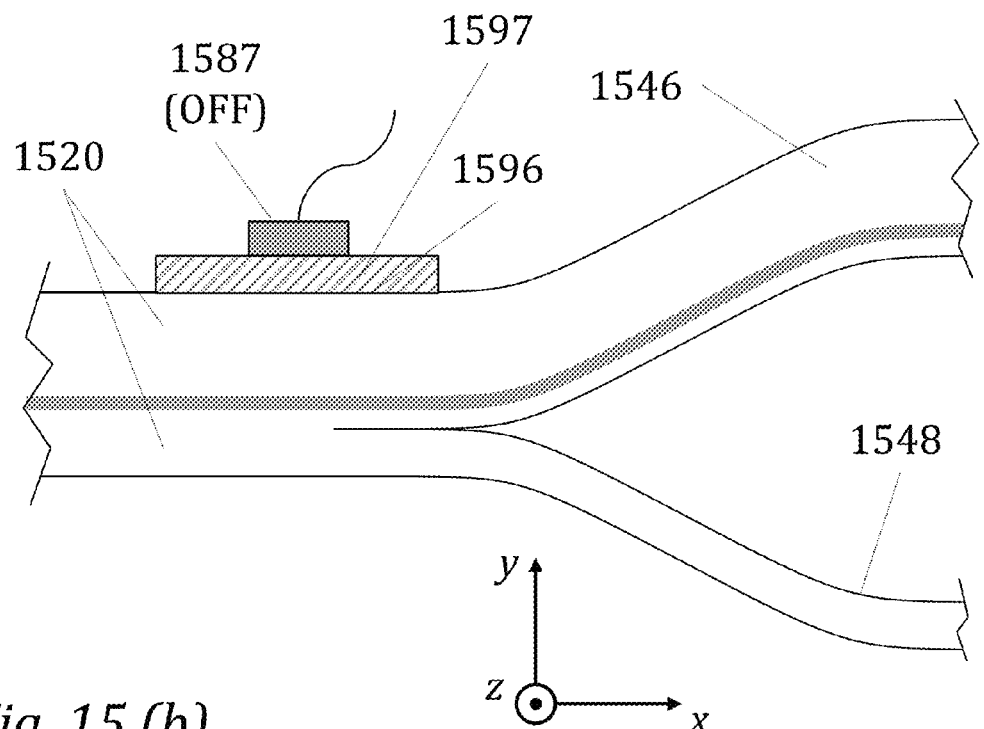
FIGS. 15(a) and (b) are schematic cross-sectional illustrations of two steps, or states, of a high-throughput particle analysis/sorting method with two sorting states and one-sided actuation.
Figure 15:
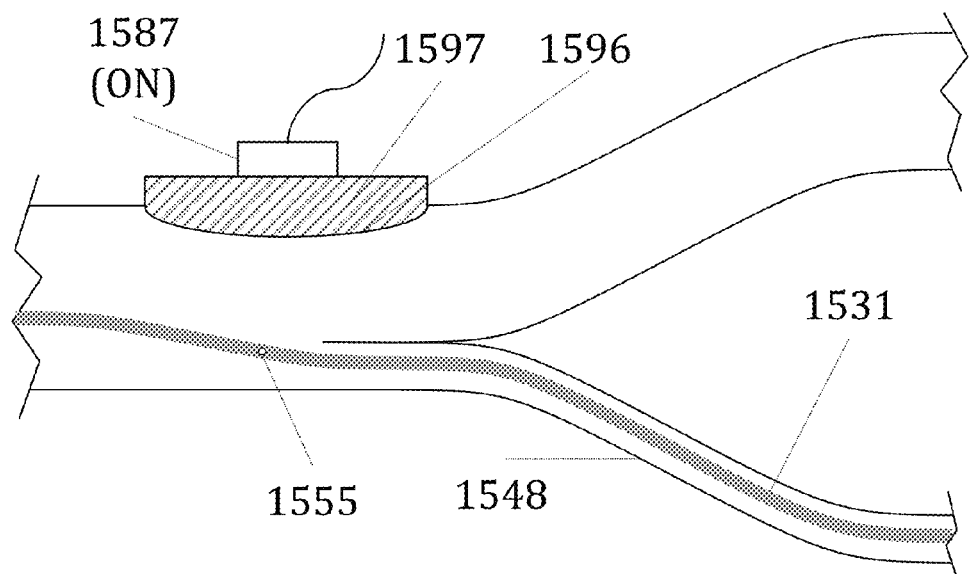

FIGS. 15(*a*) and 15(*b*) illustrate another embodiment of two states of the high-throughput sorting method of the current invention. It is similar to the embodiment illustrated in FIGS. 14(*a*) and 14(*b*), except in the design and nature of actuation. Here the actuators in the array (of which a representative element 1587 is shown in this cross-sectional view) are located in proximity to a expandable chamber 1597 adjacent to the flowcell inner wall and separated from the sheath fluid 1520 by a flexible membrane 1596. With the actuator element 1587 in the OFF or default state as shown in FIG. 15(*a*), the expandable chamber 1597 is in its default configuration at a pressure designed to match the pressure of the fluid inside the flowcell at the location of the membrane, resulting in a flat shape of the membrane to match the shape of the flowcell inner wall. With the actuator element 1587 in the ON or sorting state as shown in FIG. 15(*b*), the expandable chamber 1597 is pressurized (by means including, for instance, thermal means, mechanical means, hydraulic and gas injection means) to a higher pressure than in the default configuration; this pressure differential causes the membrane 1596 to flex into the flowcell until a new equilibrium is reached. The bulging membrane causes the flow pattern to shift in a similar way to that previously shown for FIG. 14(*b*), resulting in the shown portion 1531 of the sample core stream being diverted into the sorting channel 1548, which portion contains a particle 1555 detected upstream and automatically selected by analysis algorithms to trigger sorting actuation. Following deactivation of the depicted actuator element 1587, the expandable chamber 1597 is allowed to or made to return to its default pressure state, the membrane 1596 returns to its default flat shape, and the flow pattern returns to the original default configuration of FIG. 15(*a*).

Figure 16:
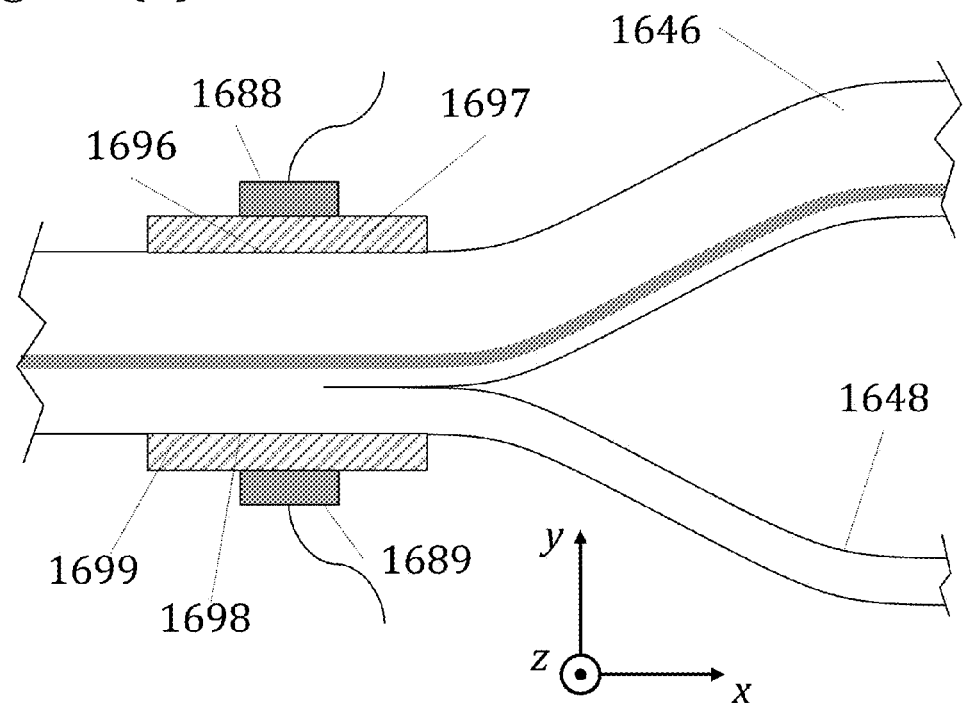
FIGS. 16(a) and (b) are schematic cross-sectional illustrations of two steps, or states, of a high-throughput particle analysis/sorting method with two sorting states and two-sided actuation.
Figure 16:
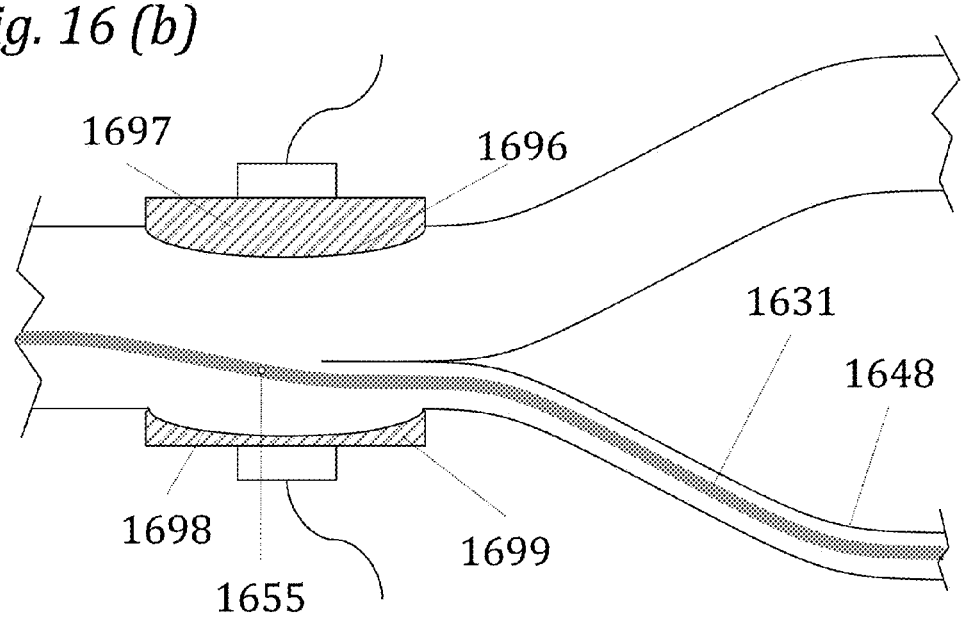

FIGS. 16(*a*) and 16(*b*) illustrate yet another embodiment of two states of the high-throughput sorting method of the current invention. It is similar to the embodiment illustrated in FIGS. 15(*a*) and 15(*b*), except in the design of actuation. Sorting actuation here is realized by means of two actuator arrays, positioned on opposite sides of the flowcell, each element of each array (of which a pair of two representative elements is shown in this cross-sectional view, element 1688 for the default-side array and element 1689 for the sort-side array) being located in proximity to expandable chambers (1697 for the default side and 1699 for the sort side) adjacent to the flowcell inner wall and separated from the sheath fluid by a flexible membrane (1696 for the default side and 1698 for the sort side). In the default state, depicted in FIG. 16(*a*), the expandable chambers 1697 and 1699 of both the default-side and sort-side actuator elements are in their default configuration at a pressure designed to match the pressure of the fluid inside the flowcell at the location of the membranes 1696 and 1698, resulting in flat shapes of the membranes to match the shape of the flowcell inner walls. In the sorting state, depicted in FIG. 16(*b*), the expandable chamber 1697 of the default-side actuator element 1688 is pressurized (by means including, for instance, heating means, mechanical means, hydraulic means, and gas injection means), through actuation, in a similar way as depicted in reference to FIG. 15(*b*); this pressure differential with respect to the local pressure in the sheath fluid causes the membrane 1696 to bulge into the flowcell until a new equilibrium is reached. Simultaneously, the expandable chamber 1699 of the sorting side actuator element 1689 is depressurized (by means including, for instance, cooling means, mechanical means, hydraulic means, and gas aspiration means), through actuation, to a lower pressure than in the default configuration; this pressure differential with respect to the local pressure in the sheath fluid causes the membrane 1698 to flex away from the flowcell until a new equilibrium is reached. The combination of the inwardly bulging default-side membrane 1696 and the outwardly flexing sort-side membrane 1698 causes the flow pattern to shift in a similar way to that previously shown for FIGS. 14(*b*) and 15(*b*), resulting in the shown portion 1631 of the sample core stream being diverted into the sorting channel 1648, which portion contains a particle 1655 detected upstream and automatically selected by analysis algorithms to trigger sorting actuation. Following deactivation of the depicted actuator element pair, both the default-side and the sort-side expandable chambers 1697 and 1699 are allowed to or made to return to their default pressure states, both the default-side and the sort-side membranes 1696 and 1698 return to their default flat shapes, and the flow pattern returns to the original default configuration of FIG. 16(*a*).

FIG. 17 is a schematic isometric depiction of the sorting region of the flowcell in an exemplary sorting state of another representative embodiment of the current invention. The configuration is similar to that depicted in reference to FIG. 13(*b*), except that instead of a single sorting channel, a plurality of sorting channels 1748 is provided along a direction z parallel to the direction of light propagation and to the major cross-sectional axis of the ribbon-like sample core stream 1730 (which is bounded by sheath fluid 1720). One advantage of this embodiment is the ability to have a plurality of different receptacles into which the sample may be sorted, depending on the location within the sample core stream 1730 where a desired particle is detected by an upstream detector array as described above in reference to FIG. 11. There may exist a relationship between some elements in the actuator array 1780 and the sorting channels 1748, whereby activation of certain actuator elements (e.g., 1787, as depicted) may correspond to diversion of the corresponding portion (e.g., 1731) of the sample core stream preferentially into one sorting channel (e.g., 1749), which portion contains a particle 1755 detected upstream and automatically selected by analysis algorithms to trigger sorting actuation; while for other elements in the actuator array, the corresponding sample core stream may be diverted partially into one sorting channel and partially into another. In the embodiment of FIG. 17, a smaller number of sorting channels 1748 is shown than the number of elements in the actuator array 1780; other embodiments of the current invention include the number of sorting channels 1748 being smaller than, equal to, or greater than the number of elements in the actuator array 1780. Also for illustrative clarity, the elements in the actuator array 1780 are shown as being adjacent to one another; other embodiments of the current invention include the elements in the actuator array being positioned so as to interpose a certain space in between each element and the ones adjacent to it.

Figure 18:
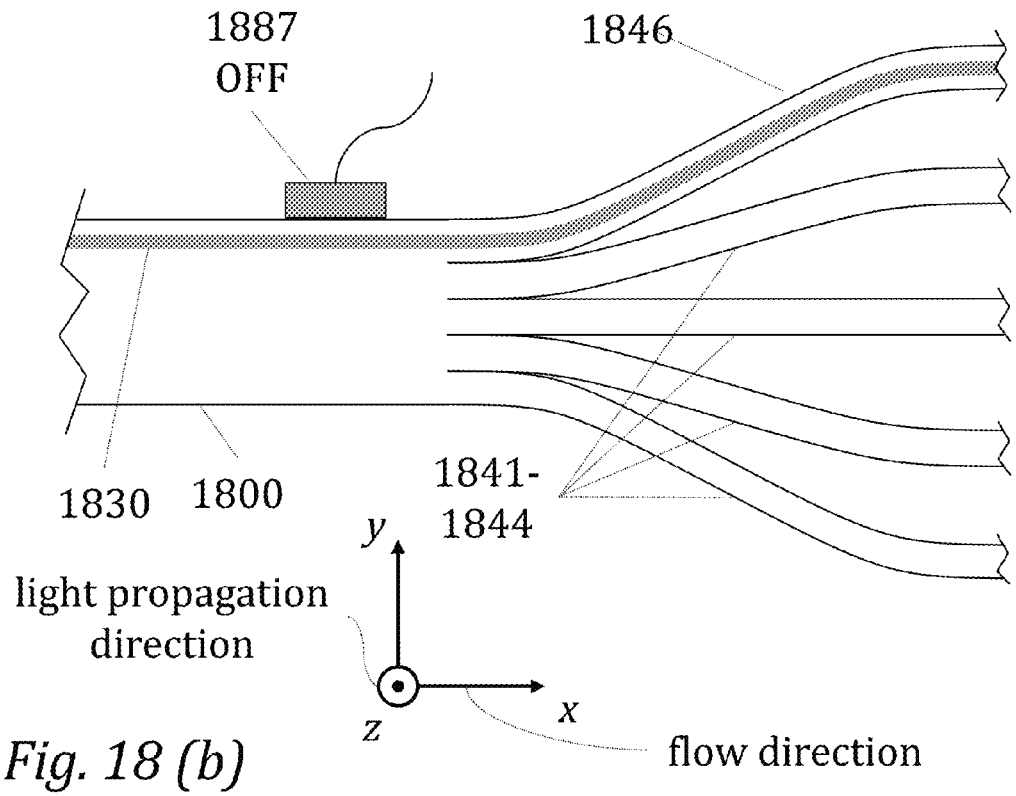
FIGS. 18(a)-(d) are schematic cross-sectional illustrations of four states of a high-throughput particle analysis/sorting method with five sorting states and one-sided actuation that uses multiple sorting channels.
Figure 18:
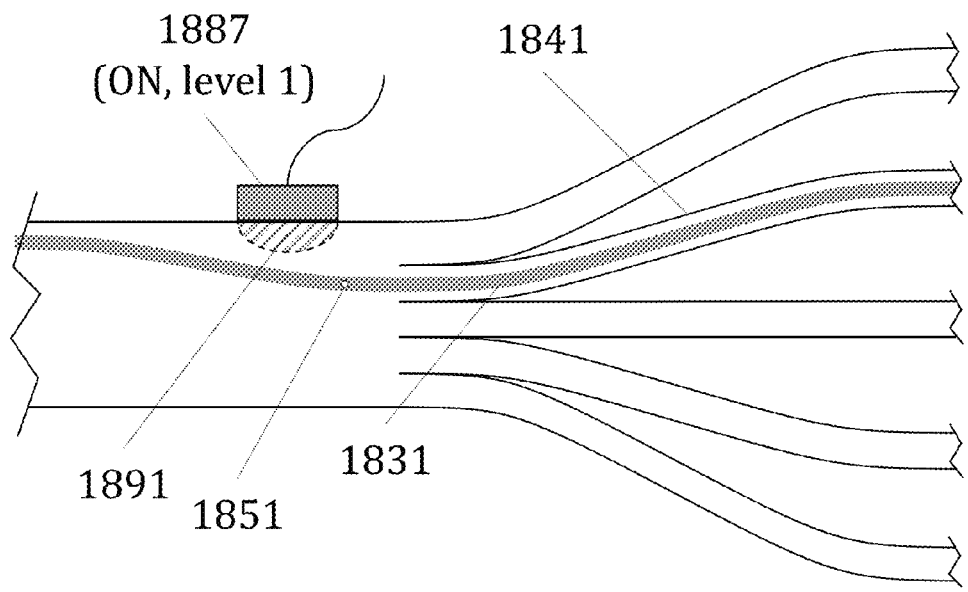
Figure 18:
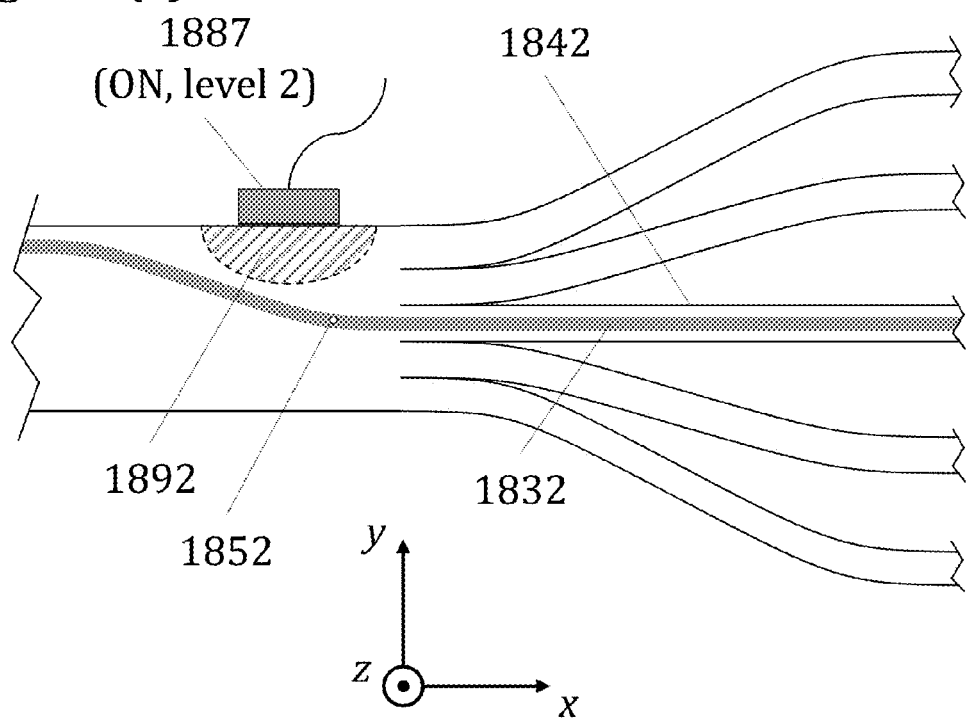
Figure 18:
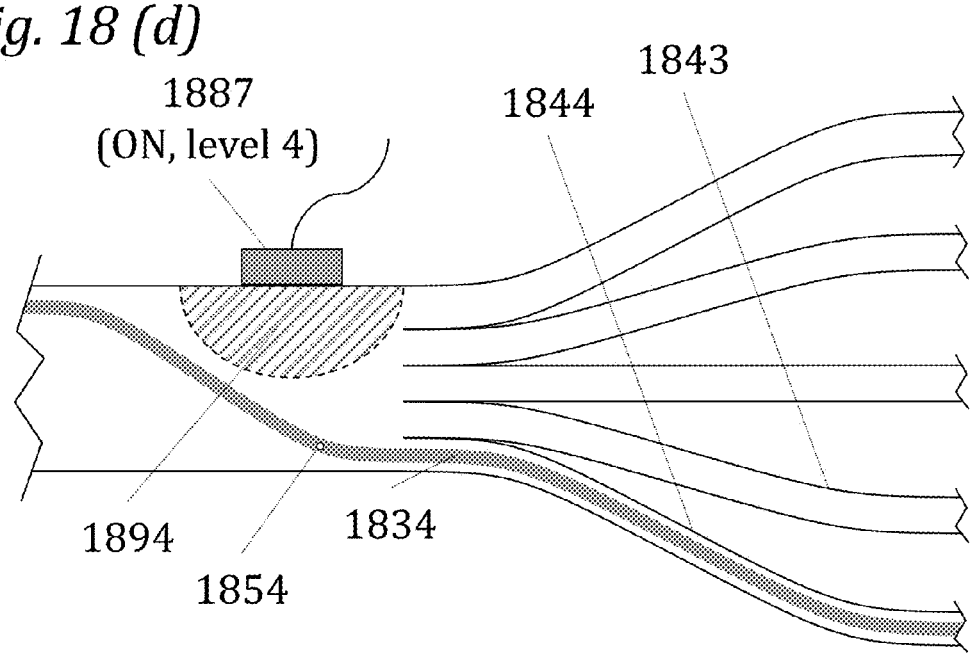

FIGS. 18(*a*)-(*d*) illustrate a multi-way sorting embodiment of the high-throughput sorting method of the current invention. Each of the four figures shows a schematic representation of a cross-sectional view of the sorting region of the flowcell. The configuration is similar to that depicted in reference to FIGS. 14(*a*) and (*b*), except that instead of a single sorting channel, a plurality of sorting channels 1841-1844 is provided along a transverse direction y. One advantage of this embodiment is the ability to have a plurality of different receptacles into which the sample may be sorted, depending on the result of the upstream analysis by the interrogating light beam, the signal detectors, and associated electronic and logic trigger circuitry. For example, the signals detected in response to the upstream interrogation of the sample may indicate that a particle, e.g., particle 1851, was detected with a certain set A of properties targeted for selection (e.g., the presence of surface antigens or intracellular markers associated with certain kinds of cancer cells). It may be desirable to sort particles having these properties into a certain collection receptacle, e.g., one provided to receive the outflow from sorting channel 1841, as illustrated in FIG. 18(b). Another particle, e.g., particle 1852, may flow past the interrogation point and produce signals that indicate the presence of a different set B of properties targeted for selection (e.g., the presence of surface antigens or intracellular markers associated with certain kinds of stem cells). It would be desirable to sort particles like particle 1852 having set-B properties into a different receptacle from that designed for collection of particles having set-A properties: e.g., a receptacle provided to receive the outflow from sorting channel 1842, as illustrated in FIG. 18(c). Likewise for yet another set D of properties, particles like particle 1854 detected as having those properties, and a sorting channel 1844 designed to flow into a receptacle to collect such particles. Accordingly, the embodiment illustrated in FIGS. 18(a)-(d) provides an example of such a multi-way sorting capability of the current invention, with a number of sorting channels 1841-1844 in addition to the default sorting channel 1846. FIGS. 18(a)-(d) exemplarily show four such sorting channels explicitly. It will be apparent to those skilled in the art that additional configurations having more or less than four sorting channels, in addition to the default sorting channel, do not depart from the scope of the disclosed invention.

Each of the sorting channels 1841-1844 (as well as the default sorting channel 1846) may optionally be connected with a receiving receptacle designed to collect the fluid flow from the respective channel. The selection of a particular sorting channel (or of the default sorting channel) as the target for reception of a desired sorted portion of the sample core stream is effected by actuation of one (or more) of the elements 1887 of an actuator array. In a two-way sort there are two principal sorting states, which can be described as OFF (default) and ON (sorting) as described above, with respect to any one of the elements in the actuator array, in relation to FIGS. 14(a)-(b), 15(a)-(b), and 16(a)-(b). In a multi-way sort, on the other hand, there generally can be as many sorting states as there are sorting "ways" or possible sorting channels. With reference to FIGS. 18(a)-(d), five possible sorting channels are indicated (the default sorting channel 1846 plus four sorting channels 1841-1844); accordingly, this is referred to as a five-way sort. An actuation process is provided to result in different degrees of deflection of the sample core stream portion, corresponding to the selection of different sorting channels.

In FIG. 18(a) an element 1887 of an actuator array is depicted as embodied in, in contact with, or in proximity of the inner wall of the flowcell 1800 on the default sorting channel side. Similarly to the state depicted in FIG. 14(a), FIG. 18(a) shows the configuration of the default state, where with the actuator element 1887 in the OFF state, the portion of the sample core stream 1830 shown in this cross-sectional view flows by design into the default sorting channel 1846. Similarly to the state depicted in FIG. 14(b), FIGS. 18(b)-(d) show the configurations of various sorting states, where with the actuator element 1887 in the ON state at levels 1, 2, and 4, respectively, transient regions 1891, 1892, and 1894, respectively (comprising, for instance, a gas, vapor, gas-vapor bubble, or a less-dense region of sheath fluid), are generated (by means including, for instance, thermal means, electrolytic means, and gas injection means), which create respective localized flow diversions in the depicted cross-sectional plane and in its immediate vicinity, which diversions deflect the portions 1831, 1832, and 1834, respectively, of the sample core stream shown in this cross-sectional view, and the corresponding particles 1851, 1852, and 1854, respectively, into the respective sorting channels 1841, 1842, and 1844. Following deactivation of the depicted actuator element, the transient gas bubble shrinks or is cleared away, and the flow pattern returns to the original default state of FIG. 18(a). Not shown is the configuration of a sorting state intermediate to the sorting states of FIGS. 18(c) and 18(d), corresponding to an actuation level 3, whereby a transient region of a size intermediate between that of regions 1892 and 1894 diverts a portion of the sample core stream shown in this cross-sectional view into sorting channel 1843.

The depictions in FIGS. 14(a), 15(a), 16(a), and 18(a) are described above as representing the default states of the sorting region of the flowcell in the respective embodiments of the current invention, in the cross-sectional plane containing the actuator element being activated. They also represent the sorting states of the sorting region of the flowcell in each of the cross-sectional planes containing the remaining actuator elements (those not being activated). In other words, the flow pattern of the sample core stream is designed to be affected mainly only locally in the vicinity of the plane containing the actuator element being activated, while the flow patterns of the sample core stream outside this plane are designed to remain mainly unaffected by such activation. FIG. 13(b) schematically summarizes this aspect of the invention.

Throughout this disclosure the term "default sorting channel" has been associated with an OFF state of an actuator or actuator element, signifying a passive state in which no particle sorting is performed, and associated parts of a core stream are typically collected and discarded as waste. The term "sorting channel" has been associated with an ON state of an actuator or actuator element, signifying an activated state of an actuator or actuator element, in which active sorting of a particle is performed. While for some embodiments this may be a preferred configuration, the invention is not so limited, and included under the scope of the invention are embodiments where a passive state of an actuator or actuator element is associated with particle collection, and an active state of an actuator or actuator element is associated with generation of a waste stream from the particle analyzer.

Figure 19:
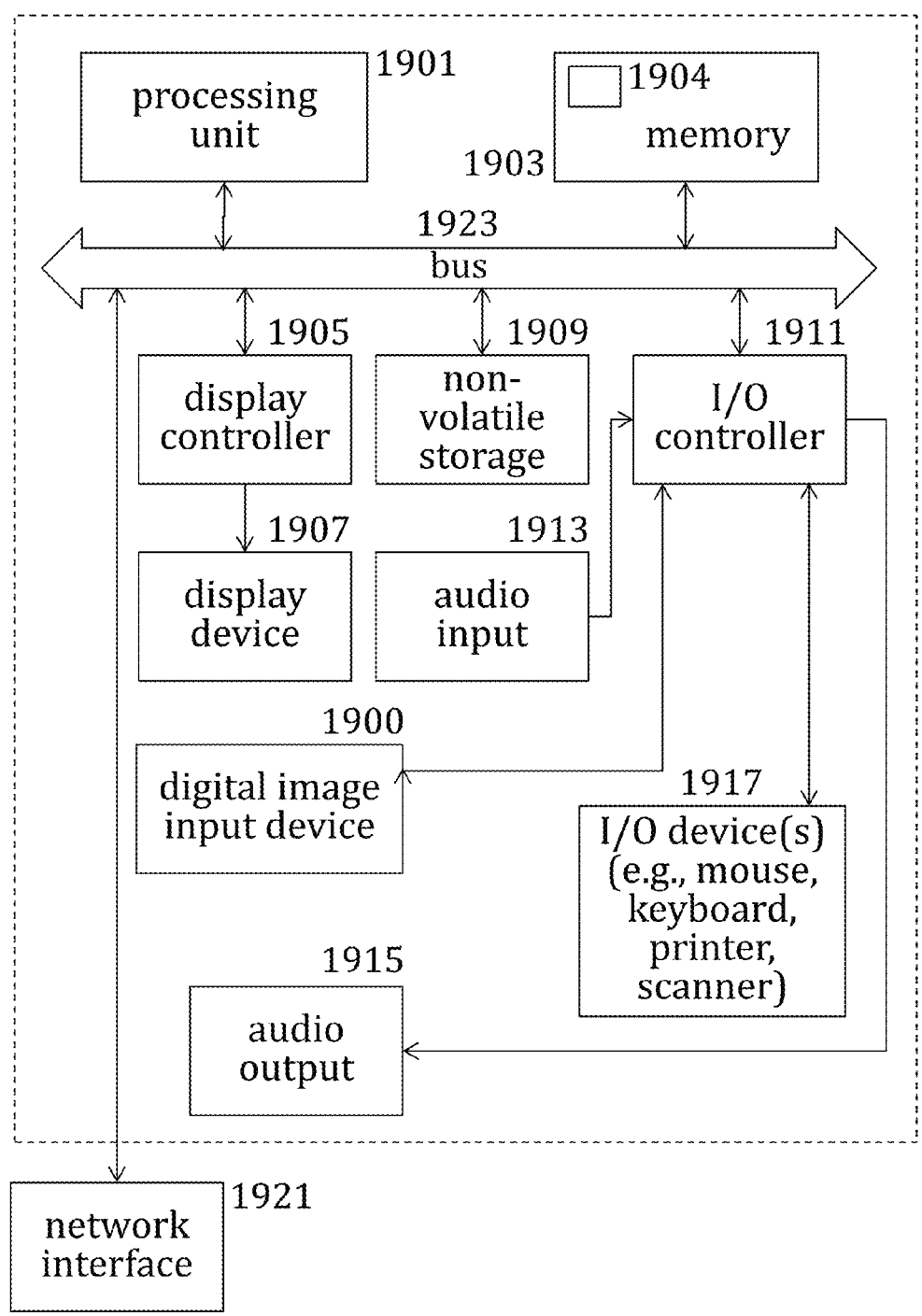
FIG. 19 is a schematic representation of a data processing system to provide a high-throughput particle analyzer/sorter.

FIG. 19 shows a block diagram of an exemplary embodiment of a data processing system 1900 to provide a high-throughput single-particle analysis and sorting system as described herein. In an embodiment, data processing system 1900 is a part of the control system to perform a method that includes forming a ribbon-like sample core stream; forming a substantially nondiffracting interrogation light beam; conveying particles in the core stream for analysis by the substantially nondiffracting light beam; providing means of sorting actuation based on such analysis; and sorting particles, as described herein. In some embodiments, data processing system 1900 is represented by any one of electronic processing units 790, 890, and 990 depicted in FIGS. 7, 8, and 9, respectively.

Data processing system 1900 includes a processing unit 1901 that may include a microprocessor or microprocessor, such as Intel microprocessor (e.g., Core i7, Core 2 Duo, Core 2 Quad, Atom), Sun Microsystems microprocessor (e.g., SPARC), IBM microprocessor (e.g., IBM 750), Motorola microprocessor (e.g., Motorola 68000), Advanced Micro Devices ("AMD") microprocessor, Texas Instrument microcontroller, and any other microprocessor or microcontroller.

Processing unit 1901 may include a personal computer (PC), such as a Macintosh® (from Apple Inc. of Cupertino, Calif.), Windows®-based PC (from Microsoft Corporation of Redmond, Wash.), or one of a wide variety of hardware platforms that run the UNIX operating system or other operating systems. For at least some embodiments, processing unit 1901 includes a general purpose or specific purpose data processing system based on Intel, AMD, Motorola, IBM, Sun Microsystems, IBM processor families, or any other processor families. As shown in FIG. 19, a memory 1903 is coupled to the processing unit 1901 by a bus 1923. Memory 1903 has instructions and data 1904 stored thereon which when accessed by processing unit 1901 cause the processing unit 1901 to perform methods to provide label free or native particle analysis, as described herein.

Memory 1903 can be dynamic random access memory ("DRAM") and can also include static random access memory ("SRAM"). A bus 1923 couples processing unit 1901 to memory 1903 and also to a non-volatile storage 1909 and to a display controller 1905 (if a display is used) and to an input/output (I/O) controller(s) 1911. Display controller 1905 controls in the conventional manner a display on a display device 1907 which can be a cathode ray tube (CRT), liquid crystal display (LCD), or any other display device. Input/output devices 1917 can include a keyboard, disk drives, printers, a scanner, a camera, and other input and output devices, including a mouse or other pointing device. I/O controller 1911 is coupled to one or more audio input devices 1913 such as, for example, one or more microphones.

Display controller 1905 and I/O controller 1911 can be implemented with conventional well-known technology. An audio output 1915 such as, for example, one or more speakers, may be coupled to I/O controller 1911. Non-volatile storage 1909 is often a magnetic hard disk, an optical disk, or another form of storage for large amounts of data. Some of this data is often written, by a direct memory access process, into memory 1903 during execution of software in data processing system 1900 to perform methods described herein.

One of skilled in the art will immediately recognize that the terms "computer-readable medium" and "machine-readable medium" include any type of storage device that is accessible by processing unit 1901. Data processing system 1900 can interface to external systems through a modem or network interface 1921. It will be appreciated that modem or network interface 1921 can be considered to be part of data processing system 1900. This interface 1921 can be an analog modem, ISDN modem, cable modem, token ring interface, satellite transmission interface, or other interfaces for coupling a data processing system to other data processing systems.

It will be appreciated that data processing system 1900 is one example of many possible data processing systems which have different architectures. For example, personal computers based on an Intel microprocessor often have multiple buses, one of which can be an input/output (I/O) bus for the peripherals and one that directly connects processing unit 1901 and memory 1903 (often referred to as a memory bus). The buses are connected together through bridge components that perform any necessary translation due to differing bus protocols.

Network computers are another type of data processing system that can be used with the embodiments as described herein. Network computers do not usually include a hard disk or other mass storage, and the executable programs are loaded from a network connection into memory 1903 for execution by processing unit 1901. A typical data processing system will usually include at least a processor, memory, and a bus coupling the memory to the processor.

It will also be appreciated that data processing system 1900 can be controlled by operating system software which includes a file management system, such as a disk operating system, which is part of the operating system software. Operating system software can be the family of operating systems known as Macintosh® Operating System (Mac OS®) or Mac OS X® from Apple Inc. of Cupertino, Calif., or the family of operating systems known as Windows® from Microsoft Corporation of Redmond, Wash., and their associated file management systems. The file management system is typically stored in non-volatile storage 1909 and causes processing unit 1901 to execute the various acts required by the operating system to input and output data and to store data in memory, including storing files on non-volatile storage 1909.

In various embodiments, hardwired circuitry may be used in combination with software instructions to implement methods described herein. A non-transitory machine readable medium can be used to store software and data which when executed by a data processing system causes the system to perform various methods described herein. This executable software and data may be stored in various places including for example ROM, volatile RAM, non-volatile memory, and/or cache. Portions of this software and/or data may be stored in any one of these storage devices.

Thus, a machine readable medium includes any mechanism that provides (i.e., stores and/or transmits) information in a form accessible by a machine (e.g., a computer, network device, or any device with a set of one or more processors, etc.). For example, a machine readable medium includes recordable/non-recordable media (e.g., read only memory (ROM); random access memory (RAM); magnetic disk storage media; optical storage media; flash memory devices; and the like).

The methods as described herein can be implemented using dedicated hardware (e.g., using Field Programmable Gate Arrays, or Application Specific Integrated Circuit) or shared circuitry (e.g., microprocessors or microcontrollers) under control of program instructions stored in a machine-readable medium. The methods as described herein can also be implemented as computer instructions for execution on a data processing system, such as system 1900 of FIG. 19.

A method of analyzing particles in a fluid using a particle analyzer is disclosed, comprising the steps of:
creating a ribbon-like core stream having a largest cross-sectional dimension;
exposing the ribbon-like core stream to a non-Gaussian, substantially nondiffracting light beam in a flowcell;
creating a signal resulting from the interaction of the non-Gaussian, substantially nondiffracting light beam with a particle in the fluid; and
detecting the signal with a detector.

A method of analyzing and sorting particles in a fluid using a particle analyzer is disclosed, comprising the steps of:
creating a ribbon-like core stream having a largest cross-sectional dimension;
exposing the ribbon-like core stream to a non-Gaussian, substantially nondiffracting light beam in a flowcell;
creating a signal resulting from the interaction of the non-Gaussian, substantially nondiffracting light beam with a particle in the fluid;
detecting the signal with a detector;
transferring the signal to a sorting actuator driver through a processing unit;
bringing a sorting actuator into a desired sorting state with the sorting actuator driver in response to the signal; and
using the desired sorting state of the sorting actuator to direct a part of the core stream with the particle to a desired sorting channel.

A method of analyzing particles in a fluid using a particle analyzer is disclosed, comprising the steps of:
creating a ribbon-like core stream having a largest cross-sectional dimension;
exposing the ribbon-like core stream to a non-Gaussian, substantially nondiffracting light beam in a flowcell;
creating a signal resulting from the interaction of the non-Gaussian, substantially nondiffracting light beam with a particle in the fluid;
detecting the signal with a detector;
wherein the detector is one of a plurality of detectors, whereby individual detectors are configured to receive a signal from a corresponding portion of the exposed ribbon-like core stream.

A method of analyzing and sorting particles in a fluid using a particle analyzer is disclosed, comprising the steps of:
creating a ribbon-like core stream having a largest cross-sectional dimension;
exposing the ribbon-like core stream to a non-Gaussian, substantially nondiffracting light beam in a flowcell;
creating a signal resulting from the interaction of the non-Gaussian, substantially nondiffracting light beam with a particle in the fluid;
detecting the signal with a detector;
transferring the signal to a sorting actuator driver through a processing unit;
bringing a sorting actuator into a desired sorting state with the sorting actuator driver in response to the signal;
using the desired sorting state of the sorting actuator to direct a part of the core stream with the particle to a desired sorting channel;
wherein the detector is one of a plurality of detectors, whereby individual detectors are configured to receive a signal from a corresponding portion of the exposed ribbon-like core stream, and
wherein the sorting actuator is one of a plurality of sorting actuators, the plurality of sorting actuators being in substantial alignment with the largest cross-sectional dimension of the ribbon-like core stream.

In the foregoing specification, embodiments of the invention have been described with reference to specific exemplary embodiments thereof. It will, however, be evident that various modifications and changes may be made thereto without departing from the broader spirit and scope of the invention. It will be clear to those skilled in the art that the combinations of the various aspects of the invention disclosed herein are encompassed in the disclosure and do not depart from the scope of the invention. For example, any of the methods and configurations disclosed in reference to actuation (e.g., the configurations shown in FIGS. 14(a) and (b), 15(a) and (b), and 16(a) and (b)) may be combined with any of the methods and configurations disclosed in reference to sorting channels (e.g., the configurations shown in FIGS. 13(a) and (b), 17, and 18(a)-(d)). Likewise, any of the methods and configurations disclosed in reference to optical collection and detection (e.g., the configurations shown in FIGS. 9, 10, and 11) may be combined with any of the actuation and sorting configurations, and any of the methods and configurations disclosed in reference to SLMs may be combined with any of the optical collection and detection, and actuation and sorting configurations. As a particular example, the combination of the sorting configuration illustrated in FIG. 17 may be combined with the sorting configuration illustrated in FIGS. 18(a)-(d) to result in a two-dimensional array of sorting channels, one dimension along direction z and one dimension along direction y, providing for a multiplicity of sorting options according to both location within the ribbon-like sample core stream and result of optical interrogation. As another example, embodiments illustrated or described herein as employing detector arrays and actuator arrays may alternatively be implemented using single-point detectors and single actuators: in this latter case, the illustrations of FIGS. 14(a) and (b), 15(a) and (b), 16(a) and (b), and 18(a)-(d) are to be taken as schematic representations of cross-sectional projections through the flowcell rather than of single cross-sectional planes; and in FIG. 13(b), actuation of the entire actuator results in the temporary sorting of the entire cross-section of the ribbon-like core stream 1330, rather than of just portion 1331, into sorting channel 1348. As yet another particular example, in some embodiments of the invention the relationship between the default sorting channel and the sorting channel (as, e.g., illustrated in FIGS. 13(a) and (b)) may be inverted, where the actuator elements of actuator array 1380 are all normally in the ON state, delivering the entire sample core stream 1330 to the sorting channel 1348; and where one or more of the actuator elements (e.g., element 1387, analogously to FIG. 13(b)) is turned OFF following triggering by the detection algorithms, delivering a desired portion 1331 of the sample core stream containing a desired particle 1355 to the default sorting channel 1346. As yet another particular example, combination of the actuator-pair structure described in reference to FIGS. 16(a) and (b) and the multiple actuation states described in reference to FIGS. 18(a)-(d) may be implemented in some embodiments with the default sorting channel in the topmost position, as shown in FIG. 18(a); and it may be implemented in other embodiments with the default sorting channel in the middle position (corresponding to channel 1842 in FIG. 18(c)), with some of the sorting states designed to divert portions of the sample core stream to channels on one side of channel 1842 (e.g., channels 1841, 1846 in FIGS. 18(a) and (b)) and some of the sorting states designed to divert portions of the sample core stream to channels on the other side of channel 1842 (e.g., channels 1843, 1844 in FIGS. 18(c) and (d)). The default sorting channel, in other words, may be designed to be any of the available sorting channels. Some embodiments of the invention employing a plurality of detectors and/or a plurality of sorting actuators may also be realized with the use of a Gaussian beam with traditional diffraction properties. The specification and drawings are, accordingly, to be regarded in an illustrative rather than a restrictive sense.

What is claimed is:

1. A particle analyzer, comprising:
   a source of a non-Gaussian, substantially nondiffracting light beam;
   a flow path configured to produce a ribbon-like core stream in a flowcell, said core stream having a cross-sectional aspect ratio of at least 4 and a largest cross-sectional dimension of at least 50 micrometers;
   said flowcell being configured to expose a segment of said core stream to said light beam; and
   a detector configured to detect a signal from said core stream, the signal resulting from an interaction of a particle in said core stream with said light beam.

2. The particle analyzer of claim 1, further comprising:
   a first sorting actuator connected with said flowcell and downstream of said segment of said core stream exposed to said light beam; and
   a plurality of sorting channels in fluid connection with said flow path and downstream of said first sorting actuator;
   said first sorting actuator having multiple actuation states, each actuation state configured to direct at least one part of said core stream to a corresponding sorting channel of said plurality of sorting channels.

3. The particle analyzer of claim 2, further comprising a second sorting actuator, said second sorting actuator being connected with said flowcell and opposite said first sorting actuator, said second sorting actuator being operable in coordination with said first sorting actuator.

4. The particle analyzer of claim 1, wherein said light beam is aligned with the largest cross-sectional dimension of said core stream under an angle of no more than 45 degrees.

5. The particle analyzer of claim 1, wherein said light beam is aligned substantially along the largest cross-sectional dimension of said core stream.

6. A particle analyzer, comprising:
   a source of a non-Gaussian, substantially nondiffracting light beam;
   a flow path configured to produce a ribbon-like core stream in a flowcell, said core stream having a cross-sectional aspect ratio of at least 4 and a largest cross-sectional dimension of at least 50 micrometers;
   said flowcell being configured to expose a segment of said core stream to said light beam; and
   a plurality of detectors, whereby individual detectors in said plurality of detectors are configured to receive a signal from a corresponding portion of said core stream, said signal resulting from an interaction of a particle in said corresponding portion of said core stream with said light beam.

7. The particle analyzer of claim 6, further comprising:
   a first plurality of sorting actuators connected with said flowcell, said first plurality of sorting actuators being positioned downstream of said segment of said core stream exposed to said light beam;
   said first plurality of sorting actuators being in substantial alignment with the largest cross-sectional dimension of said core stream; and
   a plurality of sorting channels in fluid connection with said flow path and downstream of said first plurality of sorting actuators;
   the sorting actuators of said first plurality of sorting actuators having multiple actuation states, each actuation state configured to direct at least one part of said core stream to a corresponding sorting channel of said plurality of sorting channels.

8. The particle analyzer of claim 7, further comprising a second plurality of sorting actuators, said second plurality of sorting actuators being connected with said flowcell and opposite said first plurality of sorting actuators, actuators in said second plurality of sorting actuators being operable in coordination with actuators in said first plurality of sorting actuators.

9. The particle analyzer of claim 6, wherein said light beam is aligned with the largest cross-sectional dimension of said core stream under an angle of no more than 45 degrees.

10. The particle analyzer of claim 6, wherein said light beam is aligned substantially along the largest cross-sectional dimension of said core stream.

11. A particle analyzer, comprising:
    a source of a light beam;
    a flow path configured to produce a ribbon-like core stream in a flowcell, said core stream having a cross-sectional aspect ratio of at least 4 and a largest cross-sectional dimension of at least 50 micrometers;
    said flowcell being configured to expose a segment of said core stream to said light beam; and
    a plurality of detectors, whereby individual detectors in said plurality of detectors are configured to receive a signal from a corresponding portion of said core stream, said signal resulting from an interaction of a particle in said corresponding portion of said core stream with said light beam.

12. The particle analyzer of claim 11, further comprising:
    a first plurality of sorting actuators connected with said flowcell, said plurality of sorting actuators being positioned downstream of said segment of said core stream exposed to said light beam;
    said plurality of sorting actuators being in substantial alignment with the largest cross-sectional dimension of said core stream; and
    a plurality of sorting channels in fluid connection with said flow path and downstream of said first plurality of sorting actuators;
    the sorting actuators of said first plurality of sorting actuators having multiple actuation states, each actuation state configured to direct at least one part of said core stream to a corresponding sorting channel of said plurality of sorting channels.

13. The particle analyzer of claim 12, further comprising a second plurality of sorting actuators, said second plurality of sorting actuators being connected with said flowcell and opposite said first plurality of sorting actuators, actuators in said second plurality of sorting actuators being operable in coordination with actuators in said first plurality of sorting actuators.

14. The particle analyzer of claim 11, wherein said light beam is aligned with the largest cross-sectional dimension of said core stream under an angle of no more than 45 degrees.

15. The particle analyzer of claim 11, wherein said light beam is aligned substantially along the largest cross-sectional dimension of said core stream.

* * * * *

UNITED STATES PATENT AND TRADEMARK OFFICE
CERTIFICATE OF CORRECTION

| | | |
|---|---|---|
| PATENT NO. | : 9,551,645 B2 | Page 1 of 1 |
| APPLICATION NO. | : 14/793626 | |
| DATED | : January 24, 2017 | |
| INVENTOR(S) | : Giacomo Vacca | |

It is certified that error appears in the above-identified patent and that said Letters Patent is hereby corrected as shown below:

On the Title Page

Item (74) Attorney, Agent or Firm:
After Aurora Consulting LLC please add -- ; Wouter Roorda --

Signed and Sealed this
Eighteenth Day of April, 2017

Michelle K. Lee
*Director of the United States Patent and Trademark Office*